United States Patent [19]

Atwal et al.

[11] Patent Number: 5,374,643
[45] Date of Patent: Dec. 20, 1994

[54] ARYL UREA (THIOUREA) AND CYANOGUANIDINE DERIVATIVES

[75] Inventors: Karnail S. Atwal, Newtown, Pa.; George C. Rovnyak, Hopewell, N.J.

[73] Assignee: E. R. Squibb & Sons, Inc., Princeton, N.J.

[21] Appl. No.: 103,052

[22] Filed: Aug. 12, 1993

Related U.S. Application Data

[63] Continuation of Ser. No. 944,135, Sep. 11, 1992, abandoned.

[51] Int. Cl.$^5$ .................. A61K 31/415; A61K 31/42; A61K 31/41; A61K 31/40
[52] U.S. Cl. .................................... 514/364; 514/374; 514/382; 514/378; 514/397; 514/406; 514/414; 514/456; 549/399; 549/220; 548/131; 548/236; 548/247; 548/252; 548/343.5; 548/364.4; 548/454
[58] Field of Search ............... 549/399, 220, 399; 514/456, 364, 374, 378, 382, 397, 406, 414, 456; 548/131, 236, 247, 252, 343.5, 364.4, 454

[56] References Cited

U.S. PATENT DOCUMENTS

| | | | |
|---|---|---|---|
| 5,140,031 | 8/1992 | Atwal et al. | 514/302 |
| 5,268,386 | 12/1993 | Harada et al. | 514/456 |

FOREIGN PATENT DOCUMENTS

| | | |
|---|---|---|
| 205292 | 12/1986 | European Pat. Off. |
| 214818 | 3/1987 | European Pat. Off. |
| 274821 | 7/1988 | European Pat. Off. |
| 344747 | 12/1989 | European Pat. Off. |
| 350805 | 1/1990 | European Pat. Off. |
| 359537 | 3/1990 | European Pat. Off. |
| 389861 | 10/1990 | European Pat. Off. |
| 0401010A2 | 12/1990 | European Pat. Off. |
| 412531 | 2/1991 | European Pat. Off. |
| 462761 | 12/1991 | European Pat. Off. |
| 488616 | 6/1992 | European Pat. Off. |
| 0501797A1 | 9/1992 | European Pat. Off. |
| WO8707607 | 12/1987 | WIPO |

OTHER PUBLICATIONS

H. J. Petersen et al., *J. of Med. Chem.*, vol. 21, No. 8, 1978:773–781, Washington, D.C.

V. A. Ashwood et al., "Synthesis and Antihypertensive Activity of 4-(cyclic amido)-2H-1-benzopyrans", *J. Med. Chem.*, 1986:29:2194-2201.

C. R. Rasmussen et al., "Improved Procedures of Cycloalkyl-, Arylalkyl-, and Arylthioureas", *Synthesis*, Jun. 1988:456–459.

V. V. Mozolis et al., "Preparation of N-Substituted Thiourea", *Russian Chemical Reviews*, 42(7):1973:587–595.

J. M. Evans et al., "Synthesis and Antihypertensive Activity of Substituted trans-4-Amino-3,4-dihydro-2,2-dimethyl-2H-1-benzopyran-3-ols", *J. Med. Chem.*, 1983:26:1582–1589.

R. W. Lang et al., "Synthesis of Selectivity Trifluoromethylated Pyridine Derivatives as Potential Antihypertensives", *Helvetica Chimica Acta*, 1988:71:596-601.

P. Sebok et al., "Selective Synthesis of Analogues of the Natural Prococenes Synthesis and Regioselective (-Alkylation of 6-Chloro- and 6-Tert-Buyl-7,8-Dihydroxy-2,2-Dimethyl-4-Chromanones", *Heterocycles*, 1988:27:2595–2607.

P. Teixidor et al., "Improved Preparation of Precocene II, Unexpected Results in the Reduction of Alkoxy Substituted Acetophenones and 4-Chromanones with Sodium Borohydride", *Heterocycles*, 1988:27:2459–2465.

A. Banerji et al., "Enolates of o-Hydroxyacetophenones: Novel Synthesis of 2,2-Dialkyl-4-Chromanones", *Tetrahedron Let.*, 1979:38:3685–3686.

G. Ariamala et al., "A Simple Route for the Synthesis of 4-Chlorochromenes and Chroman-4-ones", *Tetrahedron Let.*, 1988:vol. 29, No. 28:3487–3488.

R. Albrecht et al., CA77:88182j (1972), Abstract of Chim. Ther., 1972:7(1):90-13.

*Primary Examiner*—Richard L. Raymond
*Assistant Examiner*—Mary C. Cebulak
*Attorney, Agent, or Firm*—Ellen K. Park

[57] ABSTRACT

Novel compounds useful, for example, in the treatment of ischemic conditions and arrhythmia having the formula I
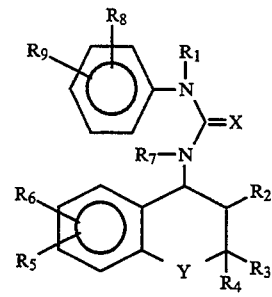
wherein X is oxygen, sulfur or —NCN and the R groups are as defined herein.
39 Claims, No Drawings

ARYL UREA (THIOUREA) AND CYANOGUANIDINE DERIVATIVES

This application is a continuation-in-part of U.S. application Ser. No. 07/944,135, filed Sep. 11, 1992, now abandoned.

FIELD OF THE INVENTION

The present invention relates to novel potassium channel activators and to a method of using these compounds as antiischemic and anti-arrhythmic agents.

SUMMARY OF THE INVENTION

In accordance with the present invention novel compounds having potassium channel activating activity and useful as antiischemic and antiarrhythmic agents are disclosed. These compounds have the general formula

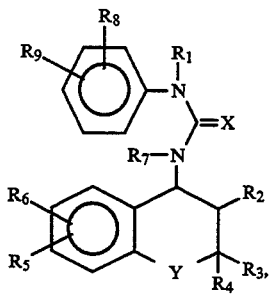
I and pharmaceutically acceptable salts thereof wherein,
X is oxygen, sulfur or —NCN;
Y is oxygen, sulfur, a single bond or

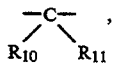

with the proviso that if one or both of $R_{10}$ and $R_{11}$ are alkyl, then $R_3$ and $R_4$ are each hydrogen and if one or both of $R_3$ and $R_4$ are alkyl, then $R_{10}$ and $R_{11}$ are each hydrogen;

$R_1$ and $R_7$ are independently hydrogen, alkyl, arylalkyl, -(alkyl)amino or -(alkyl)substituted amino;
$R_2$ is hydrogen, hydroxy or

$R_3$ and $R_4$ are each independently hydrogen, alkyl or arylalkyl; or, $R_3$ and $R_4$ taken together with the carbon atom to which they are attached form a 5- to 7-membered carbocyclic ring;
$R_5$ is hydrogen, alkyl, haloalkyl, alkenyl, alkynyl, cycloalkyl, arylalkyl, cycloalkylalkyl, —CN, —NO$_2$, —COR$^a$, —COOR$^a$, —CONHR$^a$, —CON(R$^a$)$_2$, —CF$_3$, —S—alkyl, —SOalkyl, —SO$_2$alkyl,

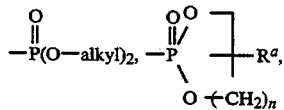

halogen, amino, substituted amino, —O-alkyl, —OCF$_3$, —OCH$_2$CF$_3$, —OCOalkyl, —OCONR$^a$alkyl, —NR$^a$COalkyl, —NR$^a$COOalkyl or —N(-R$^a$)CON(R$^a$)$_2$ wherein R$^a$ is hydrogen, alkyl, aryl, arylalkyl, cycloalkyl, (cycloalkyl)alkyl or haloalkyl;

$R_6$ is hydrogen, alkyl, halo, —OH, —O-alkyl, amino, substituted amino, —O-alkyl, —O-haloalkyl, —O-COalkyl, —OCONR$^a$alkyl, —NR$^a$COalkyl, —NR$^a$COOalkyl or —NR$^a$CON(R$^a$)$_2$;

$R_8$ is hydrogen, alkyl, —O-alkyl, —S-alkyl, halo or nitro;

$R_9$ is aryl, heterocyclo, -(alkyl)amino or -(alkyl)substituted amino; or $R_8$ and $R_9$ and the atoms to which they are attached complete a 5-to 7-membered ring which may contain one to three hetero atoms (O,S, NR$^b$), CO, SO, SO$_2$; wherein R$^b$ is hydrogen, alkyl, aryl, arylalkyl, CO-alkyl, CO-haloalkyl, CO-substituted amino; or $R_1$ and $R_7$, $R_7$ and $R_8$ or $R_1$ and $R_8$ taken together with the atoms to which they are attached form a 5- to 7-membered ring; and n is 1, 2 or 3.

DETAILED DESCRIPTION OF THE PRESENT INVENTION

Throughout the present application the following definitions apply to the terms used herein.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and at least one double bond preferably three to five carbons. The term "alkynyl" refers to straight or branched chain hydrocarbon radicals having from two to eight carbons and at least one triple bond, preferably three to five carbons.

The term "cycloalkyl" refers to saturated carbocyclic rings of 3 to 7 carbon atoms. Cyclopropyl, cyclopentyl and cyclohexyl are preferred.

The term "halo" or "halogen" refers to chlorine, bromine, fluorine and iodine.

The term "halo substituted alkyl" refers to such alkyl groups described above in which one or more hydrogens have been replaced by a halogen, such as chloromethyl, bromomethyl, trifluoromethyl, pentafluoroethyl, 2,2,2-trichloroethyl and 2,2,2-trifluoroethyl. Trifluoromethyl is preferred.

The term "aryl" refers to phenyl, 1-naphthyl, 2-naphthyl or mono substituted phenyl, 1-naphthyl, 2-naphthyl wherein said substituent is alkyl of 1 to 4 carbons, (amino)alkyl, (substituted amino)alkyl, alkylthio of 1 to 4 carbons, alkoxy of 1 to 4 carbons, halo, nitro, cyano, hydroxy, amino, —NH-alkyl wherein alkyl is of 1 to 4 carbons. —N(alkyl)$_2$ wherein alkyl is of 1 to 4 carbons, —CF$_3$, —O(haloalkyl),

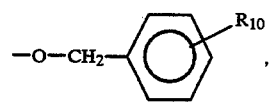

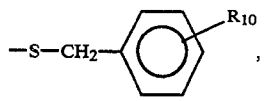

wherein R$_{10}$ is hydrogen, alkyl of 1 to 4 carbons, alkoxy of 1 to 4 carbons, alkylthio of 1 to 4 carbons, halo, hydroxy or —CF$_3$), —O—OCH$_2$-cycloalkyl, —S—CH$_2$-cycloalkyl, or -alkyl(COOR$_{11}$) (wherein R$_{11}$ is hydrogen or alkyl), and di-substituted phenyl, 1-naphthyl, 2-naphthyl wherein said substituents are selected from methyl, methoxy, methylthio, halo, —CF$_3$, nitro, amino, —OCHF$_2$, or -alkyl(COOR$_{11}$).

Preferred aryl groups include unsubstituted phenyl and monosubstituted phenyl wherein the substituent is nitro, halo, —CF$_3$, alkyl, cyano, methoxy, or —O-haloalkyl.

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available atom. Preferred monocyclic hetero groups include 2- and 3-thienyl, 2- and 3-furyl, 2-, 3- and 4-pyridyl, and imidazolyl, pyrazole, oxazole, isoxazole and oxadiazole. The term hetero also includes bicyclic rings wherein the five or six membered ring containing O,S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7benzimidazolyl, 4, 5, 6 or 7-benzoxaiazolyl, and 4, 5, 6 or 7benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, —N(alkyl)$_2$ wherein alkyl is of 1 to 4 carbons, —CF$_3$, or —OCHF$_2$ or such monocyclic and bicyclic rings wherein two or three available carbons have substituents selected from methyl, methoxy, methylthio, halo, CF$_3$, nitro, hydroxy, amino and OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkyl-alkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl substituted with alkyl, alkoxy, alkylthio, halo, trifluoromethyl or hydroxy.

The compounds of formula I wherein X is oxygen can be prepared by reacting a compound of the formula II

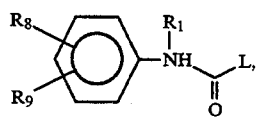

where L is a leaving or activating group, with an amine of the formula III

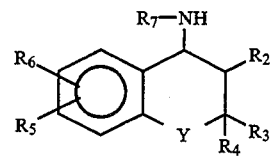

in an organic solvent, such as dimethylformamide, tetrahydrofuran, acetonitrile or dichloromethane, to provide the compounds of formula I where X is oxygen.

Suitable leaving or activating groups include chlorine or 4-nitrophenyloxy. For example, the 5-aminoindane of formula IV

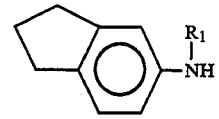

can be reacted with 4-nitrophenylchloroformate in solvents, such as methylene chloride and pyridine to provide the compound

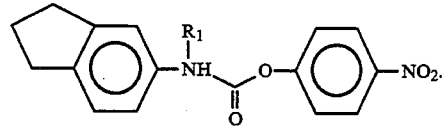

Compounds of formula I wherein X is oxygen and R$_1$ is hydrogen can also be prepared from compounds of formula III by treatment with an isocyanate of the formula V

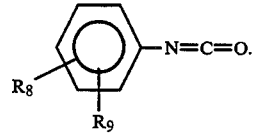

Compounds of formula I wherein X is sulfur can be prepared from compounds of formula H wherein X is oxygen by treatment with P$_2$S$_{10}$ or Lawesson's reagent.

Compounds of formula I wherein X is sulfur and R$_1$ is hydrogen can be prepared by treatment of an isothiocyanate of formula VI

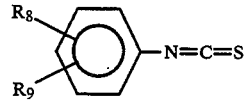

with amines of formula III.

Compounds of formula I where X is —NCN can be prepared by reacting a compound of the formula VII

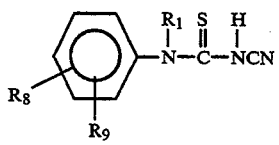

VII with the amine of formula III in the presence of a coupling agent, such as a carbodiimide, in a solvent, such as dimethylformamide, tetrahydrofuran, acetonitrile or dichloromethane. If dicyclohexylcarbodiimide is used, it should be employed with an acid source. Preferably, the carbodiimide is of the formula A

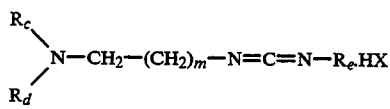

A wherein X is halogen; $R_c$, $R_d$ and $R_e$ are independently alkyl, cycloalkyl, phenyl, phenylalkyl or cycloalkylalkyl; or $R_c$ and $R_d$ together with the N-atom form 1-pyrrolidinyl, 1-piperidinyl, 4-morpholinyl, 4-thiomorpholinyl, 4-alkyl-1-piperazinyl or 4-phenylalkyl-1-piperazinyl. Most preferably the carbodiimide is 1-(3-dimethylaminopropyl)-3-ethyl-carbodiimide hydrochloride.

Compounds of formula VII wherein $R_1$ is hydrogen are readily prepared by reacting a compound of the formula VI with monosodiumcyanamide, in a solvent, such as methanol. Compounds of formula I wherein X is —NCN and $R_2$ is trans-hydroxyl can also be prepared from compounds of formula I wherein X is sulfur by first converting them to compounds of formula IX

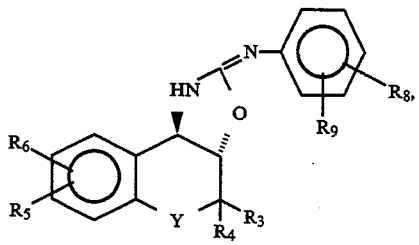

IX by treatment with a carbodiimide such as dicyclohexylcarbodiimide or 1-(3-diethylaminopropyl)-3-ethyl carbodiimide in an organic solvent such as acetonitrile and dimethylformamide.

Compounds of formula IX are then treated with cyanamide in the presence of an organic base such as triethylamine to provide compounds of formula I where X is —NCN and $R_2$ is trans-hydroxy.

Compounds of formula I where in $R_2$ is

can be prepared from compounds of formula I wherein $R_2$ is hydroxy by treatment with an acid chloride of formula X

X in the presence of an organic base such as pyridine or triethylamine.

The aminoalcohol of formula III wherein $R_2$ is trans-hydroxy can be prepared by methods described in the literature, such as by J. M. Evans, C. S. Fake, T. C. Hamilton, R. H. Poyser, E. A. Watts, *J. Med. Chem.*, 1983, 26, 1582 and *J. Med. Chem.*, 1986, 29, 2194; R. W. Lang, P. F. Wenk, *Helvetica Chimica Acta*, 1988, 71,596; EP 0205292 A2 (1986), and WO 87/07607. The amino alcohol of formula III where $R_2$ is cis-hydroxy can be prepared by methods described by G. Burrell, J. M. Evans, G. E. Jones and G. Stemp, *Tetrahedron Letters*, Vol. 31, p. 3649 (1990).

Amines of formula III wherein Y is a single bond can be prepared according to D. R. Buckle et at., (*Journal of Medicinal Chemistry*, 1991, Vol. 34, p. 919). Amines of formula III wherein Y is $CH_2$ can be prepared by methods described in V. A. Ashwood et al., (*J. Med. Chem.*, 1991, Vol. 34, p. 3261).

The amine of formula III, wherein $R_2$ is hydrogen, can be prepared from a ketone of the formula XI

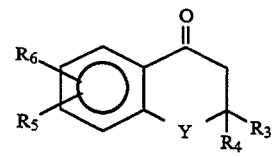

XI by standard methodology. The ketone of formula IX can be obtained by literature procedures, such as disclosed by P. Sebok and T. Timar, *Heterocycles*, 1988, 27, 2595; P. Teixidor et at., *Heterocycles*, 1988, 27, 2459; A. Benerji and N. C. Goomer, *Tetrahedron Letters*, 1979, 3685; G. Ariamala and K. K. Subramanian, *Tetrahedron Letters*, Vol. 29, No. 28, p. 3487–3488 (1988).

The amine of formula III wherein $R_2$ is hydrogen, can also be prepared from olefins of the formula XII

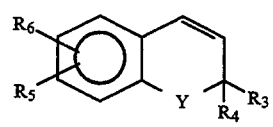

XII by a sequence of steps which involve: (a) catalytic hydrogenation of the double bond, (b) bromination of the resulting compound with N-bromosuccinimide and light, (c) displacement of the bromide with azide using sodium azide followed by (d) catalytic reduction of the azide.

The olefin of formula XII can be prepared from the ketone of formula XI by reduction (sodium borohydride) and dehydration (p-toluenesuffonic acid).

For the preparation of individual enantiomers of compounds of formula I the enantiomers of amine ffl can be prepared and reacted as described above. To prepare enantiomers of amine III wherein $R_2$ is trans-hydroxy and Y is oxygen, the olefin of formula X is epoxidized with commercial bleach using a chiral manganese catalyst XIII

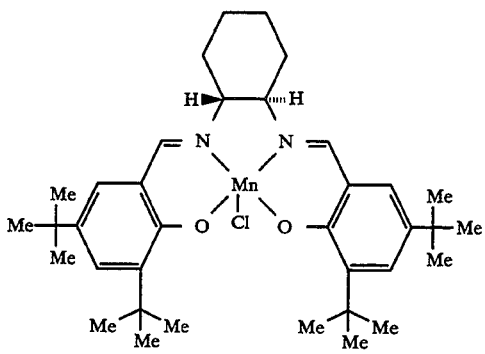

XIII as described by N. H. Lee et al. (*Tetrahedron Letters*, 1991, V. 32, p. 5055–5058), to provide predominantly the chiral epoxide of formula XIV or XV, depending on the chirality of the 1,2-diaminocyclohexane used in formula XIII.

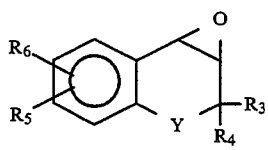

XIV

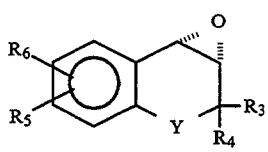

XV

The epoxides of formula XIV and XV can be reacted with an amine of formula $R_7NH_2$ to provide enantiomers of amine III wherein Y is oxygen and $R_2$ is trans-hydroxy as known in the art.

For the preparation of enantiomers of other compounds of formula I, the amine of formula III is converted to diastereomeric amides of formula XVI and XVII

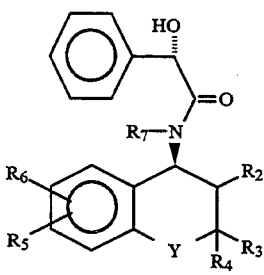

XVI

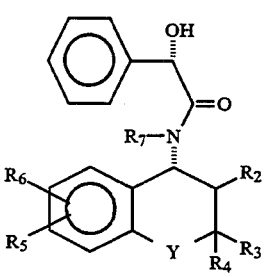

XVII by treatment with chiral nonracemic mandelic acid in the presence of dicyclohexylcarbodiimide.

Compounds of formula XVI and XVII are separated by crystallization or chromatography as known in the art.

The enantiomer of mandelic acid that yields crystalline amide with the desired stereochemistry is preferred in the resolution step.

Compounds XVI and XVII are then hydrolyzed by heating in dioxane in the presence of sulfuric acid to give enantiomers of formula XVIII and XIX.

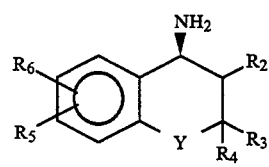

XVIII

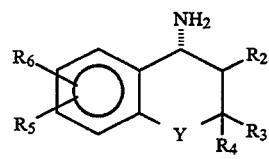

XIX

The compounds of the present invention can have asymmetric centers at carbons 2–4 of the bicyclic ring. Also, any one of the R's can have an asymmetric carbon. Consequently, compounds of formula I can exist in diastereomeric forms or in mixes thereof. The above described process can utilize racemates, enantiomers or diastereomers as starting materials. When diastereomeric products are prepared, they can be separated by conventional chromatographic or fractional crystallization methods.

The compounds of the present invention wherein $R_7$ and $R_1$ are each hydrogen can exist as a mixture of tautomers represented by the following structures. The tautomeric products are obtained in relative amounts that differ from compound to compound. All forms are included in the scope of formula I including formula I'

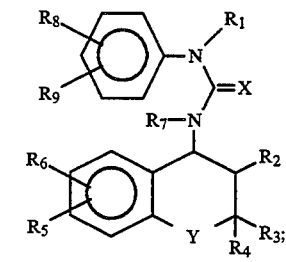

I'

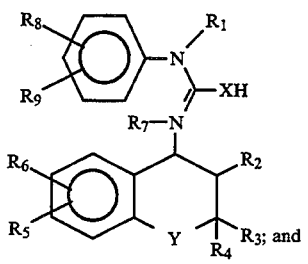

I''

-continued

I'''

Preferred compounds are those wherein $R_1$ is hydrogen or -(alkyl)amino or -(alkyl)substituted amino;

$R_2$ is hydrogen or hydroxy;

$R_3$ and $R_4$ are each alkyl;

$R_5$ is an electron withdrawing group;

$R_6$ is hydrogen, alkyl or O-alkyl;

$R_7$ is hydrogen;

$R_8$ is heterocyclo, -(alkyl)amino, -(alkyl)substituted amino or aryl;

$R_9$ is hydrogen; or $R_8$ and $R_9$ form a 5- to 6-membered ring.

Most preferred are those compounds wherein $R_1$ is hydrogen or $CH_2CH_2NMe_2$;

$R_2$ is trans-hydroxy;

$R_3$ and $R_4$ are each methyl;

$R_5$ is —CN or —$NO_2$;

$R_6$ is hydrogen;

$R_7$ is hydrogen or $CH_2CH_2NMe_2$;

$R_8$ is oxazole, tetrazole, oxadiazole, methyloxadiazole, isoxazole, dimethylpyrazole or $CH_2N(Me)CH_2Ph$;

$R_9$ is hydrogen; or $R_8$ and $R_9$ and the atoms to which they are attached complete an indane ring which may contain one to three hetero atoms.

The compounds of formula I and the pharmaceutically acceptable salts act as potassium channel activators. Thus, compounds of the present invention are useful cardiovascular agents, for example, as anti-arrhythmic agents or antiischemic agents.

As described previously, compounds of formula I are particularly useful as antiischemic agents since they have been found to possess little or no antihypertensive activity. Thus, compounds of formula I are useful for the treatment of ischemic conditions, e.g. myocardial ischemia, cerebral ischemia, lower limb ischemia, i.e., peripheral vascular disease, and the like. The selectivity, i.e.. antiischemic activity with little or no antihypertensive activity, means that in the treatment of, for example, ischemic heart disease, these compounds are less likely to cause coronary steal, profound hypotension and coronary underperfusion. By little or no vasodilation activity is meant that these compounds have $IC_{50}$ (rat aorta) values greater than that of the potassium channel activator, cromakalim.

The "selective" antiischemic agents typically are those having $IC_{50}$ (rat aorta) values >10 times that of cromakalim (i.e., have 1/10 the vasodilatory action) and preferably those having $IC_{50}$ values >50 times that of cromakalim.

Thus, for example, by the administration of a composition containing one (or a combination) of the compounds of this invention, ischemic conditions of a mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular and non-cardiovascular uses.

As a result of the potassium channel activating activity of compounds of this invention, these compounds are also useful in the treatment of other cardiovascular disorders. For example, compounds of the present invention are useful as therapy for congestive heart failure, as anti-anginal agents, as anti-fibrillatory agents, and in limiting myocardial infarction.

Compounds of the present invention are additionally expected to be useful in the treatment of central nervous system disorders (e.g., Parkinsonism, as anti-tremor agents, epilepsy).

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin convening enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase. prourokinase, and anisoylated plasminogen streptokinase activator complex (APSAC, Eminase, Beecham Laboratories), or calcium channel blocking agents such as nifedipine or dilfiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carder, excipient, binder, preservative, stabilizer, flavor, etc., in a unit dosage form as called for by accepted pharmaceutical practice. The amount of active substance in these compositions or preparations is such that a suitable dosage in the range indicated is obtained.

Specific embodiments of the present invention are described hereinafter in the following examples.

EXAMPLE 1

(3S-trans)-3-(6-Cyano-3,4-dihydro-3-hydroxy-2,2-dimethyl-2H-1-benzopyran-4-yl)-N'-(2,3-dihydro-1-H-inden-5yl)urea A. (1aR-cis)-1a,7b-Dihydro-2,2-dimethyl-2H-oxireno[c][1]benzopyran-6-carbonitrile A solution of 0.05M $Na_2HPO_4$ (10 mL) was added to a solution of undiluted commercial household bleach (25 mL). Sodium hydroxide (1N solution) was added dropwise to the resulting solution (0.55M in NaOCl) until pH~11.3. This solution was cooled to 0° C. and then added to cold (0° C.) solution of Mn (III) salon complex (0.26 g, 0.4 mmol, described by N. H. Lee et al., Tetrahedron Letters, 1991, V 32, p. 5055) and 6-cyano-2,2-dimethyl-2H-1-benzopyran (1.85 g, 10 mmol, prepared according to Evans et al., J. Med. Chem., 1985, 29, p. 2194 and J. Med. Chem., 1983, 26, p. 1582) in dichloromethane (10 mL). The two phase reaction mixture was stirred at 0° C. and monitored by TLC. After eight hours, the heterogeneous brown mixture was filtered through a pad of celite and the organic phase was separated. It was washed with brine (50 mL), dried over anhydrous magnesium sulfate and concentrated in vacuo to yield a light yellow solid (2.0 g, 99%). The solid was recrystallized from aqueous ethanol to give (1aR-cis)-1a,7b-dihydro-2,2-dimethyl-2H-oxireno-[c][1]benzopyran-6-carbonitrile as a white solid (0.6 g), m.p. 128°-133° C. $^1$HNMR (CDCl$_3$) δ7.58 (d, J=2.3 Hz, 1H), 7.46 (dd, J=2.3 & 1.7 Hz 1H), 6.79 (d, J=8.2 Hz, 1H), 3.84(d, J=4.1 Hz, 1H), 3.47 (d, J=4.1 Hz, 1H), 1.53(s,3H), 1.22 (s,3H). $^{13}$CNMR(CDCl$_3$) δ156.4, 134.4, 133.8, 121.1,119.0, 118.7 104.2, 74.6, 62.2, 49.8, 25.4, 22.9. $[\alpha_D]^{25}$=+80.7° (c=1.166, MeOH).

Analalysis calculated for C$_{12}$H$_{11}$NO$_2$·0.09 H$_2$O: C, 71.05; H, 5.56; N, 6.91; Found: C, 71.18; H, 5.39; N, 6.78.

B.   (3S-trans)-4-Amino-3,4-dihydro-3-hydroxy-2,2-dimethyl-2H-1-benzopyran-6-carbonitrile To a solution of (1aR-cis)-1a,7b-dihydro-2,2-dimethyl-2H-oxireno-[c][1]benzopyran-6-carbonitrile (3.0 g, 15.0 mmol, compound of example 1, part A) in ethanol (30 mL) and tetrahydrofuran (30 mL) was added ammonium hydroxide (30 mL) and the reaction mixture was heated at 50° C. in a pressure bottle for 16 hours. Most of the solvent was evaporated and the residue was dissolved in 1N hydrochloric acid. It was extracted with ether and the organic extracts were discarded. The aqueous layer was made basic by the addition of 1N sodium hydroxide and extracted with chloroform. The combined organic extracts were washed with brine and dried over anhydrous magnesium sulfate. The solvent was evaporated to yield (3S-trans)-4-amino-3,4-dihydro-3-hydroxy-2,2-dimethyl-2H- 1-benzopyran-6-carbonitrile (2.8 g), as a colorless foam. This material was used for the next reaction without further purification.

C. 4[[[(4-Nitrophenyl)oxy]carbonyl]amino]indane

To a suspension of 5-aminoindane (2.75 g, 20 mmol) in methylene chloride (50 mL) under argon was added pyridine (0.79 g, 10 mmol) followed by a solution of 4-nitrophenylchloroformate (4.0 g, 20.0 mmol) in methylene chloride (30 mL). The reaction mixture was allowed to stir at room temperature for 24 hours. The solid was filtered and washed with ethyl ether to give 4[[[(4-nitrophenyl)oxy]carbonyl]amino]indane (4.0 g) as a light yellow solid.

D.   (3S-trans)-3-(6-Cyano-3,4-dihydro-3-hydroxy-2,2-dimethyl-2H-1-benzopyran-4-yl)-N'-(2.3-dihydro-1-H-inden-5-yl)urea A solution of (trans)-4-amino-3,4-dihydro-3-hydroxy-2,2-dimethyl-2H-1-benzopyran-6-carbonyl (1.0 g, 4.6 mmol, prepared according to Example 1, part B) in dimethylformamide (10 mL) under argon was treated with 4[[[(4-nitrophenyl)oxy]carbonyl]amino]indane (2.0 g, 6.9 mmol, prepared according to Example 1, part C) and the reaction was heated at 80° C. for five hours. The reaction mixture was poured into water (100 mL) and the product that precipitated out was filtered off. The product was crystallized from ethanol to give (3S-trans)-N-(6-cyano-3,4-dihydro-3-hydroxy-2,2-dimethyl-2H-1-benzopyran-4-yl)-N'-(2,3-dihydro-1-H-inden-5-yl)urea as a colorless solid (0.6 g), m.p. 235°-237° C.: $^1$H NMR (DMSO-d$_6$) δ8.50 (s, 1H), 7.60 (m,2H), 7.10 (m,2H), 6.90 (d, J=8.2 Hz, 1H), 6.54 (d, J=8.2 Hz, 1H), 5.70 (d, J=5.9 Hz, 1H), 4.66 (t, J=8.8 & 17.6 Hz, 1H), 3.60 (dd, J=5.9 & 15.3 Hz, 1H), 2.8 (m, 5 H), 1.99 (t, J=7.6 & 14.6 Hz, 2H), 1.42 (s, 3H), 1.19 (s, 3H); $^{13}$C NMR (DMSO-d$_6$) 156.2, 156.0, 144.1, 138.4, 136.4, 132.7, 132.4, 126.1, 125.2, 124.1, 122.8, 119.1, 117.9, 116.2, 115.8, 102.6, 80.3, 71.5, 49.3, 32.5, 31.6, 26.5, 25.2, 18.9; IR (KBr) 1204.7, 1489.1, 1551.9, 1723.3, 2224.2, 2942.2, 3354.4 cm$^{-1}$, $[\alpha]^{25}_D$=7.5° (c=.867, DMF).

Analalysis calculated for C$_{22}$H$_{23}$N$_3$O$_3$: C, 68.95; H, 6.22; N, 10.97; Found: C, 69.12; H, 5.86; N, 10.80.

EXAMPLE 2

(3S-trans)-N''-Cyano-N-(6-cyano-3,4-dihydro-3-hydroxy-2,2-dimethyl-2H-1-benzopyran-4-yl-N'-[4-(2.3-dihydro-1H-inden-5-yl)]guanidine A. N-Cyano-N'-[4-indanenyl]thiourea The suspension of monosodium cyanamide (1.3 g, 20.3 mmol) in absolute ethanol (50 mL) was slowly treated with 4-indane isothiocyanate (3.3 g, 20.3 mmol). The reaction mixture was allowed to stir at room temperature for one hour and then heated at 75° C. for eight hours. The reaction mixture was concentrated in vacuo and triturated with ethyl ether to give N-cyano-N'-[4-indanenyl]thiourea (3.5 g).

B.   (3S-trans)-N''-cyano-N-(6-cyano-3,4-dihydro-3-hydroxy-2,2-dimethyl-2H-1-benzopyran-4-yl)-N'-[4-(2,3-dihydro-1H-inden-5-yl)]guanidine The solution of N-cyano-N'-[4-indanenyl]-thiourea (1.2 g, 6.0 mmol, prepared according to part A) and (3S-trans)-4-amino-3,4-dihydro-3-hydroxy-2,2-dimethyl-2H-1-benzopyran-6-carbonitrile (1.0 g, 4.6 mmol, prepared according to Example 1, part B) in dimethylformamide (15 mL) under argon was treated with 1-(3-dimethyl-aminopropyl)-2-ethylcarbodiimide hydrochloride (1.3 g, 6.9 mmol). The reaction mixture was sintered at room temperature for two hours and then partitioned between pH 4-buffer and ethyl acetate. The aqueous phase was reextracted with ethyl acetate and the combined extracts were washed with water (4×200 mL), sodium bicarbonate and brine. After drying over anhydrous magnesium sulfate, the solvent was evaporated and the residue was purified by flash chromatography eluting with a mixture of ethyl acetate/hexanes (7:3) to yield a colorless solid (0.6 g). The solid was crystallized from ethyl acetate-hexanes to give (3S-trans)-N''-cyano-N-(6-cyano-3,4-dihydro-3-hydroxy-2,2-dimethyl-2H-1-benzopyran-4-yl)-N'-[4-(2,3-dihydro-1H-inden-5-yl)]guanidine, m.p. 163°-167° C. (with foaming): $^1$H NMR (DMSO-d$_6$) δ9.18 (s, 1H), 7.58 (m, 2H), 7.41 (m, 1H), 7.20 (m, 2H), 7.06 (d, J=8.2 Hz, 1H), 6.90 (d, J=8.8 Hz, 1H), 5.9 (s, 1H), 4.90 (t, J=8.8 & 18.2 Hz, 1H), 3.70 (t, J=6.5 & 15.3 Hz, 1H), 2.81 (dd, J=7.0 & 22.2 Hz, 4H), 2.01 (t, J=7.0 & 14.7 Hz, 2H), 1.40, 1.18 (s, 3H each); $^{13}$C NMR (DMSO-d$_6$) 161.3, 158.2, 146.5, 142.6, 137.1,134.5, 134.3. 126.9, 126.4, 124.4, 122.5, 121.0, 119.7, 119.2, 104.5, 82.3, 72.7, 53.6, 34.3, 33.7, 28.5, 27.1, 20.5; IR (KBr) 1126.3, 1267.4, 1383.3, 1489.7, 1578.2, 2182.8, 2974.2, 3345.4 cm$^{-1}$, $[\alpha]_D^{25}$=−16.9° (c=1.0, DMF).

Analalysis calculated for $C_{23}H_{23}N_5O_2 \cdot 0.32\ H_2O$: C, 67.95; H, 5.85; N, 17.20; Found: C, 68.29; H, 5.92; N, 16.76.

EXAMPLE 3

(3S-trans)-N-(6-Cyano-3,4-dihydro-3-hydroxy-2,2-dimethyl-2H-benzopyran-4-yl)-N'-[4-(1H-tetrazol-5-yl)phenyl]urea A. [4-(1H-Tetrazol-5-yl)phenyl]carbamic acid, 4-nitrophenyl ester A solution of [4-(1H-tetrazol-5-yl)phenyl]amine (0.97 g, 0.006 mol, prepared in sequence by the procedures described by W. G. Finnegan et al., *J. Amer. Chem. Soc*, 1958, 80, 3908 and McManus and Herbst, *J. Amer. Chem. Soc.*, 1959, 24, 1044) in acetonitrile (30 mL), dimethylformamide (7 mL) and pyridine (0.97 mL, 0.95 g, 0.012 mol) under argon at 0° C. was treated with p-nitrophenyl chloroformate (1.21 g, 0.006 mol) and stirred at room temperature overnight. The reaction mixture was concentrated in vacuo and an effort was made to partition the remaining oil between ethyl acetate and 1M HCl, resulting in separation of product insoluble in either phase. This was collected, triturated with wet ether and dried in vacuo overnight to yield 1.37 g of [4-(1H-tetrazol-5-yl)phenyl]carbamic acid, 4-nitrophenyl ester, m.p. >260° C. TLC, silica gel, EtOAc/MeOH/HOAc (20:1:0.2), $R_f=0.63$; $^1$H-NMR (DMSO-$d_6$) $\delta$7.6 (d, J=8.8 Hz, 2H), 7.7 (d, J=8.8 Hz, 2H), 8.1 (d, J=8.8 Hz, 2H) 8.3 (d, J=8.8 Hz, 2H); $^{13}$C-NMR (DMSO-$d_6$) $\delta$150.6, 144.7, 140.9, 128.0, 125.3, 123.0, 118.9, 118.2. M.S., (M+H)+ at 327, M.W. 326.

B. (3S-trans)-N-(6-Cyano-3,4-dihydro-3-hydroxy-2,2-dimethyl-2H-1-benzopyran-4-yl)-N'-[4-(1H-tetrazol-5,yl)phenyl]urea A mixture of (3S-trans)-4-amino-3,4-dihydro-3-hydroxy-2,2-dimethyl-2H-1-benzopyran-6-carbonitrile (0.65 g, 0.003 mol, from Example 1, part B) and [4-(1H-tetrazol-5-yl)phenyl]carbonic acid, 4-nitrophenyl ester (1.08 g, 0.0033 mol, from part A) in acetonitrile (35 mL) and dimethylformamide (20 mL) was stirred at 80° for two hours. The reaction mixture was concentrated in vacuo and the residue, diluted with ethyl acetate, was washed with 0.5M HCl, water and brine. A yellow solid that separated during the brine wash was collected and triturated with ethyl acetate to give a white solid. The organic layer was dried over magnesium sulfate, concentrated in vacuo and the residue was triturated with ethyl acetate to give additional product. The two crops were combined, triturated with water, wet ether and anhydrous ether to give 0.41 g of the title B compound, m.p. 232°-233° C. TLC, silica gel, EtOAc/MeOH/HOAc (20:1:0.2), $R_f=0.53$; $^1$H-NMR (DMSO-$d_6$) $\delta$1.2 (s, 3H), 1.4 (s, 3H), 2.5 (s, 1H), 3.6 (dd, J=5.3 & 5.3 Hz, 1H), 4.7 (dd, J=8.8 & 8.8 Hz, 1H), 5.7 (d, J=5.9 Hz, 1H), 6.7 (d, J=8.2 Hz, 1H), 6.9 (d, J=8.8 Hz, 1H), 7.6 (s, 1H), 7.7 (d, J=8.2 Hz, 2H), 7.9 (d, J=8.8 Hz, 2H), 9.4 (s, 1H); $^{13}$C-NMR (DMSO-$d_6$) $\delta$156.3, 155.5, 143.1, 132.6, 132.5, 127.8, 125.8, 119.1, 117.9, 115.9, 102.6, 80.4, 71.3, 49.4, 26.5, 18.9; IR (KBr) 2982, 2938, 2874, 2228, 1659, 1613 cm$^{-1}$. M.S., (M+H)+ at 406, M.W. 405. $[\alpha]_D = +68.0°$ (c=0.80 DMSO).

Analalysis calculated for $C_{20}H_{19}N_7O_3 \cdot 0.70\ H_2O$: C, 57.47: H, 4.92: N, 23.45; Found: C, 57.33; H, 4.91; N, 23.59.

EXAMPLE 4

(3S-trans)-N-(6-Cyano-3,4-dihydro-3-hydroxy-2,2-dimethyl-2H-1-benzopyran-4-yl)-N'-[3-(1H-tetrazol-5-yl)phenyl]urea A. 3-(1H-Tetrazol-5-yl)phenylcarbamic acid. 4-nitrophenyl ester A solution of [3-(1H-tetrazol-5-yl)phenyl]amine (0.97 g, 0.006 mol) in acetonitrile (25 mL), dimethylformamide (3 mL) and pyridine (0.97 mL, 0.95 g, 0.012 mol) under argon at 0° was treated with p-nitrophenyl chloroformate (1.21 g, 0.006 mol) and was stirred at room temperature overnight The reaction mixture was concentrated in vacuo and an effort was made to partition the remaining oil between ethyl acetate and 1M HCl, resulting in separation of a pink solid insoluble in either phase. The solid was sintered off and the organic layer was dried over magnesium sulfate, concentrated in vacuo to give additional product The two crops were combined, triturated with wet ether and dried in vacuo to yield 1.52 g of 3-(1H-tetrazol-5-yl)phenylcarbamic acid, 4-nitrophenyl ester, m.p. 186°-188° C. TLC, silica gel, EtOAc/MeOH/HOAc (20:1:.2), $R_f=0.65$; M.S. (M+H)+ at 327, M.W. 326. This material was used without further purification.

B. (3S-trans)-N-(6-Cyano-3,4-dihydro-3-hydroxy-2,2-dimethyl-2H-1-benzopyran-4- yl)-N'-[3-(1H-tetrazol-5-yl)phenyl]urea A mixture of (3S-trans)-4-amino-3,4-dihydro-3-hydroxy-2,2-dimethyl-2H-1-benzopyran-6-carbonitrile (0.65 g, 0.003 mol, from Example 1, part B) and [3-(1H-tetrazol-5-yl)phenylcarbamic acid, 4-nitrophenyl ester (1.08 g, 0.0033 mol, from part A) in acetonitrile (35 mL) and dimethylformamide (20 mL) was stirred at 80° C. for two hours. The reaction mixture was concentrated in vacuo and the residue, diluted with ethyl acetate, was washed with 0.5M HCl and water. The organic layer was concentrated in vacuo, and the residue was azeotroped with toluene and triturated with ethyl acetate/hexane (1:1). The product was purified by flash chromatography (EM-60 flash silica gel, 300 mL) and eluted with EtOAc/MeOH/HOAc (20:1:0.06). The solvent was removed in vacuo, acetic acid was azeotroped with toluene and the product was triturated in hexane (40 mL) and ethyl acetate (0.5 mL) and dried in vacuo to give 0.72 g (60%) of the title compound, m.p. 204°-208° C. TLC, silica gel, EtOAc/MeOH/HOAc (20:1:0.2), $R_f=0.58$; $^1$H-NMR (DMSO-$d_6$) $\delta$1.3 (s, 3H), 1.5 (s, 3H), 3.7 (d, J=9.4 Hz, 1H), 4.8 (dd, J=8.8 & 8,8 Hz, 1H), 5.8 (s, 1H), 6.8 (d, J=8.2 Hz, 1H), 7.0 (d, J=8.8 Hz, 1H), 7.5 (m, 5H), 8.4 (s, 1H), 9.0 (s, 1H); $^{13}$C-NMR (DMSO-$d_6$) $\delta$5 156.6, 156.0. 141.6, 132.9, 132.8, 130.2, 126.2, 125.0, 120.7, 120.1, 119.4, 118.2, 116.5, 103.0, 80.7, 71.6, 49.8, 26.9, 21.4, 19.3; IR (KBr) 2980, 2932, 2228, 1663 cm$^{-1}$. M.S., (M+H)+ at 406, M.W. 405; [60 ]D= −41.6° (c=0.76 DMSO).

Analalysis calculated for $C_{20}H_{19}N_7O_3 \cdot 0.3\ CH_3COOC_2H_5$: C, 58.96; H, 4.99; N, 22.70; Found: C, 58.72; H, 4.95; N, 22.49.

Example 5

(3S-trans)-N-(6-Cyano-3,4-dihydro-3-hydroxy-2,2-dimethyl-2H-1-benzopyran-4-yl)-N'-[3-(1,2,4-oxadiazol-5-yl)phenyl]urea A. [3-(1,2,4-oxadiazol-5-yl)]phenylcarbamic acid, 4-nitrophenyl ester A solution of 3-(1,2,4-oxadiazol-5-yl)phenyl amine (0.97 g, 0.006 mol, prepared in sequence by the procedures described in Lin et al. *J. Org. Chem.*, 1979, 44, 4160 and Lin et al., *J. Org. Chem.*, 1979, 44, 4160) in acetonitrile (25 mL) and pyridine (0.97 mL, 0.95 g, 0.012 mol) under argon at 0° C. was treated with p-nitrophenyl chloroformate (1.21 g, 0.006 mol) and was stirred at room temperature overnight. The reaction mixture was concentrated in vacuo and an effort was made to partition the remaining oil between ethyl acetate and 10% citric acid, resulting in separation of a solid, insoluble in either phase. The solid was collected and triturated with anhydrous ether and dried in vacuo to yield 1.54 g of [3-(1,2,4-oxadiazol-5-yl)]phenylcarbamic acid, 4-nitrophenyl ester, m.p. 195°–197° C. TLC, silica gel, EtOAc/MeOH (20:1), $R_f$=0.75; M.S. (M+H)+ at 327, M.W. 326. This compound contained minor impurities and was used without further purification.

B. (3S-trans)-N-(6-Cyano-3,4-dihydro-3-hydroxy-2,2-dimethyl-2H-1-benzopyran-4-yl)-N'-[3-(1,2,4-oxadiazol-5-yl)phenyl]urea A mixture of (3S-trans)-4-amino-3,4-dihydro-3-hydroxy-2,2-dimethyl-2H-1-benzopyran-6-carbonitrile (0.65 g, 0.0030 mol, from example 1, part B) and [3-(1,2,4-oxadiazol-5-yl)]phenylcarbamic acid, 4-nitrophenyl ester (1.08 g, 0.0033 mol) in acetonitrile (25 mL) and dimethylformamide (20 mL) was stirred at 80° C. for one hour. The reaction mixture was concentrated in vacuo and the residue, diluted with ethyl acetate, was washed with 10% citric acid and water. The organic layer was dried over MgSO$_4$ and concentrated in vacuo. The product was purified by flash chromatography (Sorbisol C 60 flash silica gel, 400 mL) and eluted with Hexane/EtOAc (2:1) and Hexane/EtOAc (1:1). The solvent was removed in vacuo, to give a solid that was triturated with anhydrous ether and dried in vacuo to yield 1.08 g of the title compound, m.p. 168°–170° C. TLC, silica gel, EtOAc/Hexane(2:1), $R_f$=0.42. $^1$H-NMR (DMSO-d$_6$) δ9.1 (s, 1H), 9.0 (s, 1H), 8.5 (s, 1H), 7.5 (m, 4H), 7.0 (d, J=8.8 Hz 1H), 6.8 (d, J=8.8 Hz, 1H), 5.7 (d, J=5.9 Hz, 1H), 4.7 (t, J=8.8 Hz, 1H), 3.7 (dd, J=5.9 & 3.5 Hz, 1H), 3.4 (s, 1H), 1.5 (s, 3H), 1.2 (s, 3H); $^{13}$C-NMR (DMSO-d$_6$) δ174.8, 158.6, 156.3, 155.7, 141.4, 132.6, 132.5, 130.0, 125.9, 123.7, 122.3, 120.6, 119.1, 117.9, 116.7, 102.7,1 80.4, 71.3, 49.5, 26.6, 18.9; IR (KBr) 2228, 1667, 1574, 1551, 1489 cm$^{-1}$.M.S. (M+H)+ at 406, M.W. 405; [α]$_D$=−55.20° (c=0.86 DMSO).

Analalysis calculated for C$_{21}$H$_{19}$N$_5$O$_4$.0.17 H$_2$O: C, 61.74; H, 4.77; N, 17.14; Found: C, 62.00; H, 4.75; N, 16.88.

EXAMPLE 6

(3S-trans)-N-(6-Cyano-3,4-dihydro-3-hydroxy-2,2-dimethyl-2H-1-benzopyran-4-yl)-N'-[4-(1,2,4-oxadiazol-5-yl)phenyl]urea A. 4-Aminophenyl oxadiazole A mixture of 4-nitrophenyloxadiazole (2.87 g, 0.015 mol, prepared according to Lin et al., *J. Org. Chem.*, 1979, 44, 4160) and SnCl$_2$.2H$_2$O (16.92 g, 0.075 mol) in 75 mL of ethyl acetate was heated at 75° C. for 30 minutes. The yellow reaction mixture was cooled to room temperature, poured into ice-water and the pH was made slightly basic (pH 7–8) by the addition of 5% NaHCO$_3$. The reaction mixture was then extracted with ethyl acetate, dried over MgSO$_4$ and concentrated in vacuo. The remaining yellow solid was triturated with hexane, collected and dried to yield 2.07 g of the title A compound, m.p. 97°–99° C. TLC, silica gel, EtOAc/hexanes (2:1), $R_f$=0.55; M.S. (M+H)+ at 162, M.W. 161. This compound was used without further purification.

B. 4-(1,2,4-oxadiazol-5-yl)phenylcarbamic acid, 4-nitrophenyl ester

A solution of 4-aminophenyl oxadiazole (0.97 g, 0.006 mol, compound of part A) in acetonitrile (25 mL)/DMF (2 mL) and pyridine (0.50 mL, 0.48 g, 0.006 mol) under argon at 0° C. was treated with p-nitrophenyl chloroformate (1.21 g, 0.006 mol) and was stirred at room temperature overnight. The reaction mixture was concentrated in vacuo and an effort was made to partition the remaining oil between ethyl acetate and 10% citric acid, resulting in separation of a solid insoluble in either phase. The solid was collected and triturated with anhydrous ether and dried in vacuo to yield 1.67 g of the title compound, m.p. 210°–212° C. TLC, silica gel, EtOAc/hexanes (2:1), $R_f$=0.58; M.S. (M+H)+ at 327, M.W. 326. This compound contained minor impurities and was used without further purification.

C. (3S-trans)-N-(6-Cyano-3,4-dihydro-3-hydroxy-2,2-dimethyl-2H-1-benzopyran-4-yl)-N'-[4-(1,2,4-oxadiazol-5-yl)phenyl]urea A mixture of (3S-trans)-4-amino-3,4-dihydro-3-hydroxy-2,2-dimethyl-2H-1-benzopyran-6-carbonitrile (0.65 g, 0.0030 mol, compound of Example 1, part B) and the compound of title B (1.37 g, 0.0042 mol) in acetonitrile (20 mL) and dimethylformamide (30 mL) was heated at 80° C. for two hours. The reaction mixture was concentrated in vacuo and the residue, diluted with ethyl acetate, was washed with 10% citric acid and water. The organic layer was dried over MgSO$_4$ and concentrated in vacuo. The product was purified by flash chromatography (Sorbisol C 60 flash silica gel, 400 mL) and eluted with hexanes/EtOAc (2:1) and hexanes/EtOAc (1:1). The solvent was removed in vacuo, to give a solid that was triturated with anhydrous ether and dried in vacuo to yield 0.75 g (70%) of the title compound, m.p. 162°–167° C. TLC, silica gel, EtOAc/hexanes (2:1), $R_f$=0.34. $^1$H-NMR (DMSO-d$_6$) δ9.2 (s, 1H), 9.0 (s, 1H), 8.0 (d, J=8.8 Hz, 2H), 7.7 (d, J=8.8 Hz, 2H), 7.6 (m, 2H), 7.0 (d, J=9.4 Hz, 1H), 5 6.8 (d, J=8.8 Hz, 1H), 5.7 (s, 1H), 4.7 (t, J=8.8 Hz, 1H), 3.7 (dd, J=5.9 & 3.5 Hz, 1H), 1.4 (s, 3H), 1.2 (s, 3H); $^{13}$C-NMR (DMSO-d$_6$) δ174.6, 158.4, 156.3, 155.4, 145.0, 132.6, 129.0, 125.7, 119.1, 117.9, 117.8, 115.7, 102.7, 80.4, 71.3, 49.5, 26.5, 18.9; IR (KBr) 2226, 1672, 1603, 1539, 1462 cm$^{-1}$ M.S. (M+H)+ at 406, M.W. 405; [α]$_D$=−76.2° (c=0.86 DMSO).

Analalysis calculated for C$_{21}$H$_{19}$N$_5$O$_4$.0.2 EtOAc: C, 61.90; H, 4.91; N, 16.56; Found: C, 61.85; H, 4.46; N, 16.41.

EXAMPLE 7

(3S-trans)-N-(6-Cyano-3,4-dihydro-3-hydroxy-2,2-dimethyl-2H-1-benzopyran-4-yl)-N'-[3-[3-methyl-(1,2,4-oxadiazol-5-yl)]phenyl]urea A. [3-[3-methyl(1,2,4-oxadiazol-5-yl)]phenyl]-carbamic acid, 4-nitrophenyl ester A solution of 3-[3-methyl(1,2,4-oxadiazol-5-yl)]phenyl amine (1.00 g, 5.7 mmol, prepared in sequence by the procedures described by Lin et al., *J. Org. Chem.*, 1979, 44, 4160 and Bellamy and Ou, *Tetrahedron Letters*, 1984, 25, 839) in acetonitrile (25 mL) and pyridine (0.46 mL, 0.45 g, 5.7 mmol) under argon at 0° C. was treated with p-nitrophenyl chloroformate (1.15 g, 5.7 mmol) and was stirred at room temperature overnight. The reaction mixture was concentrated in vacuo and an effort was made to partition the remaining oil between ethyl acetate and 10% citric acid, resulting in separation of a solid insoluble in either phase. The solid was collected, triturated with hexane and dried in vacuo to yield 1.59 g (82%) of the title compound, m.p. 217°–220° C. TLC, silica gel, EtOAc/MeOH/HOAc (20:1:.2), $R_f$=0.75; M.S. (M+H)+ at 341, M.W. 340. This material contained minor impurities and was used without further purification.

B. (3S-trans)-N-(6-Cyano-3,4-dihydro-3-hydroxy-2,2-dimethyl-2H-1-benzopyran-4-yl)-N'-[3-[3-methyl(1,2,4-oxadiazol-5-yl)-phenyl]urea A mixture of (3S-trans)-4-amino-3,4-dihydro-3-hydroxy-2,2-dimethyl-2H-1-benzopyran-6-carbonitrile (0.65 g, 3.0 mmol, from Example 1, part B) and [3-[3-methyl(1,2,4-oxadiazol-5-yl)]phenyl]carbamic acid, 4-nitrophenyl ester (1.12 g, 3.3 mmol, title A compound) in acetonitrile (20 mL) and dimethyl-formamide (40 mL) was stirred at 80° C. for two hours. The reaction mixture was concentrated in vacuo and the residue, diluted with ethyl acetate, was washed with 10% citric acid and water. The organic layer was dried over $MgSO_4$ and concentrated in vacuo. The product was purified by flash chromatography (Sorbisol C 60 flash silica gel, 400 mL) and eluted with Hexane/EtOAc (1:1). The solvent was removed in vacuo, to give a solid that was triturated in hexane and dried in vacuo to yield 1.10 g of the title compound, m.p. 157°–161 ° C. TLC, silica gel, EtOAc/Hexane(2:1), $R_f$=0.41. $^1$H-NMR (DMSO-$d_6$) δ9.1 (s, 1H), 8.4 (s, 1H), 7.5 (m, 5H), 6.9 (d, J=9.4 Hz, 1H), 6.8 (d, J=8.2 Hz, 1H), 5.7 (d, J=5.9 Hz, 1H), 4.7 (t, J=8.8 Hz, 1H), 3.7 (dd, J =5.9 & 4.1Hz, 1H), 2.4 (s, 3H), 1.4 (s, 3H), 1.2 (s, 3H); $^{13}$C-NMR (DMSO-$d_6$) δ174.9, 167.6, 156.3, 155.6, 141.4, 132.6, 132.5, 130.0, 125.9, 123.8, 122.1, 120.4, 119.1, 117.9, 116.6, 102.76, 80.4, 71.2, 49.5, 26.5, 18.9, 11.3; IR (KBr) 2980, 2228, 1670, 1574, 1553, 1489 cm$^{-1}$. M.S. (M+H)+ at 420, M.W. 419; $[\alpha]_D$=−43.6° (c=0.77 DMSO).

Analalysis calculated for $C_{22}H_{21}N_5O_4 \cdot 0.2\ H_2O$: C, 62.46; H, 5.10; N, 16.56; Found: C, 62.79; H, 5.10: N, 16.23.

EXAMPLE 8

(3S-trans)-N-(6-Cyano-3,4-dihydro-3-hydroxy-2,2-dimethyl-2H-1-benzopyran-4-yl)-N'-[3-(1.3-oxazol-5-yl)]phenylurea .

A. 2-(3-Nitrophenyl)-1.3-oxazole

To a solution of 3-nitrobenzoyl chloride (6.31 g, 34.0 mmol) in 30 mL of sulfolane under argon at room temperature was added 2-(trimethylsiyl)1,2,3-triazole (5.2 g, 36.8 mmol, prepared according to Washbume, *J. Organometallic Chem.*, 1976, 121,285), resulting in a very slight exothermic reaction (~35°). The mixture was heated at 140° C. for three hours, then poured into 150 mL of water and extracted with ether (2×150 mL). The ether extracts were washed with water and brine, dried (MgSO$_4$) and concentrated in vacuo to give 6.8 g of a solid. Crystallization from ether/hexane afforded the title A compound (3.9 g), m.p. 94°–95.5° C. An additional 1.8 g of the product was obtained from the mother liquors by flash chromatography (elution with 1:7 ethyl acetate/hexanes) for a total of 5.7 g. TLC, ethyl acetate/hexanes (2:1 ), $R_f$=0.47. $^{13}$H-NMR (CDCl$_3$) δ160.0, 149.0, 140.1. 136.1, 132.3, 130.4, 129.3, 125.2, 121.7. m/s (m+H)+@ 191, MW=190.

B. 2-(3-Aminophenyl)1,3-oxazole

To a slurry of stannous chloride dihydrate (11.8 g, 0.05 mol in 35 mL of ethyl acetate under argon at room temperature was added 2-(3-nitro-phenyl)1,3-oxazole (1.95 g, 0.01 mol, from part A). After heating at 80° C. for 20 minutes, the mixture was poured onto crushed ice and made basic (pH 8.5) with saturated sodium bicarbonate. After filtering the resulting solution through a pad of celite to remove insolubles, the organic layer was separated, washed with water and brine, dried (anhydrous magnesium sulfate) and concentrated in vacuo to give 1.64 g of an oil that slowly solidified. $^{13}$C-NMR (CDCl$_3$) δ162.1,146.8, 138.3, 129.7, 128.2, 117.0, 116.5, 112.5. m/s (m+H)+@ 161; MW=160.

C. N-[3-(1,3-Oxazol-2-yl)phenyl]carbamic acid 4-nitrophenyl ester

To a solution of 2-(3-aminophenyl)1,3-oxazole (1.64 g, 0.010 mol, compound of part B) in 20 mL of acetonitrile/pyridine (3:1) under argon at 0° C. was added 4-nitrophenylchloroformate (2.1 g, 0.0105 mol). The ice bath was removed and the mixture was stirred for two hours, whereupon TLC indicated disappearance of the starting material. Volatiles were removed in vacuo and the residue treated with 1N HCl to precipitate a solid that was collected, washed with water and partially air dried. Trituration of the crude solids with ethyl acetate for 24 hours and filtration afforded the title C compound (2.0 g), m.p. 169°–170° C. $^{13}$C-NMR (CDCl$_3$) δ160.5, 155.4, 150.6, 144.7, 140.2, 138.9, 129.9, 128.5, 127.6, 125.2, 122.9, 120.8. 120.5, 115.8. TLC, ethyl acetate/hexane (2:1 ), $R_f$=0.42.

D. (3S-trans)-N-(6-cyano-3,4-dihydro-3-hydroxy-2,2-dimethyl-2H-1-benzopyran-4-yl)-N'-[3-(1.3-oxazol-2-yl)phenyl]urea A solution of N-[3-(1,3-oxazol-2-yl)phenyl]-carbamic acid 4-nitrophenyl ester (1.0 g, 3.0 mmol, from part C) and (3S-trans)-4-amino-3,4-dihydro-3-hydroxy-2,2-dimethyl-2H- 1-benzopyran-6-carbonitrile (0.67 g, 3.0 mmol, described in example 1, pan B) in dry acetonitrile/dimethyl-formamide (3:1) under argon was heated at 75° C. for 0.5 hour. Volatiles were removed in vacuo and the residue, dissolved in ethyl acetate, was washed with 1N HCl, water and brine, dried over anhydrous magnesium sulfate and concentrated in vacuo to give 1.5 g of an oil. Flash chromatography on 250 mL of Sorbisil flash silica gel and elution with ethyl acetate (1:1) gave a solid (1.1 g) which was triturated with hexane/ethyl acetate (20:1 ) to give the title compound (1.0 g) as a colorless solid, m.p. 130°–135° C. (foam). $^1$H-NMR (CDCl$_3$) δ8.00 (s, 1H), 7.93 (s, 1H), 7.67 (s, 1H), 7.64 (s, 1H), 7.51 (d, J=7.0 Hz, 1H), 7.13–7.39 (m, 3H), 7.08 (s, 1H), 6.73 (d, J=8.2 Hz, 1H), 6.26 (d, J=7.62 Hz, 1H), 4.88 (t, J=8.8 Hz, 1H), 3.60 (t, J=10.0 Hz, 1H), 1.41 (s, 3H), 1.19 (s, 3H). $^{13}$C-NMR (CDCl$_3$) δ161.8, 157.4, 157.0, 139.1, 138.9, 132.9, 132.5, 129.6, 127.8, 127.4, 123.5, 121.8, 121.1,119.4, 118.4, 117.2, 103.2, 80.3, 50.6, 26.4, 18.6.

Analalysis calculated for $C_{22}H_{20}N_2O_4 \cdot 0.23\ H_2O$: C, 64.68; H, 5.05; N, 13.71; Found: C, 64.84; H, 5.33, N, 13.27.

EXAMPLE 9

N''-Cyano-N-(6-cyano-3,4-dihydro-2,2-dimethyl-2H-1-benzopyran-4-yl)-N'-(2.3-dihydro-1H-inden-5-yl)guanidine

A. 6-Cyano-3,4-dihydro-2.2-dimethyl-2H-1-benzopyran

A solution of 6-cyano-2,2-dimethyl-2H-1-benzopyran (5.5 g, 29.7 mmol, prepared according to Evans et al., *J. Med. Chem.*, 1983, 26, 1582 and *J. Med Chem.*, 1986, 29, 2194) in anhydrous ethanol (40 mL) was treated with 10% palladium over charcoal (0.35 g) and stirred under $H_2$ for two hours. The catalyst was filtered through Celite and the filter cake washed with ethyl acetate. The filtrate was concentrated under vacuum to obtain 5.71 g of a yellow oil. The crude product was dissolved in ethyl acetate (60 mL) and washed successively with 5% HCl solution (60 mL), saturated $NaHCO_3$ solution (60 mL), saturated NaCl solution (60 mL) and dried over $MgSO_4$. The solvent was recovered under vacuum to yield 5.14 g (92.4%) of the title compound as a yellow solid which crystallized on standing, m.p. 30°-31° C.

Analalysis calculated for $C_{12}H_{13}NO$: C, 76.98; H, 7.00; N, 7.48; Found: C, 77.03; H, 7.02, N, 7.58.

B. 4-Bromo-6-cyano-3,4-dihydro-2,2-dimethyl-2H-1-benzopyran

To a solution of 6-cyano-3,4-dihydro-2,2-dimethyl-2H-1-benzopyran (6.40 g, 34.18 mmol), title A compound, in carbon tetrachloride (90 mL) was added N-bromosuccinimide (6.69 g, 37.6 mmol). The solution was purged with argon. A solution of Azobisisobutyronitrile (0.4 g, 3.42 mmol) in carbon tetrachloride (10 mL) was added; the reaction was heated at reflux for 30 minutes with irradiation (high intensity visible light). The reaction mixture was concentrated under vacuum and the residue was dissolved in 75 mL ethyl acetate. The solution was washed successively with distilled water (4×75 mL), saturated sodium bicarbonate solution (75 mL), saturated NaCl solution (75 mL), and dried over magnesium sulfate. The solvent was recovered under vacuum to obtain an orange waxy solid which was triturated with cold pentane to provide a beige solid (7.19 g). This was crystallized from ethyl acetate and hexanes (10:90) to yield the title compound (4.60 g) as off-white needles, m.p. 94°-95° C. The mother liquors were combined and chromatographed on silica gel during with hexane/ethyl acetate (19:1) to afford additional product (2.26 g) for a combined yield of 75.4%.

Analalysis calculated for $C_{12}H_{12}NOBr$. C, 54.16; H, 4.54; N, 5.26; Br, 30.02; Found: C, 54.55; H, 4.62; N, 5.46; Br, 29.86.

C. 4-Azido-6-cyano-3,4-dihydro-2,2-dimethyl-2H-1-benzopyran

A solution of 4-bromo-6-cyano-3,4-dihydro-2,2-dimethyl-2H-1-benzopyran (6.73 g, 25.29 mmoles), title B compound, in dry N,N-dimethylformamide (100 mL) was treated with sodium azide (3.79 g, 50.57 mmoles) and stirred at room temperature under argon for four hours. The reaction mixture was partitioned between 100 mL ethyl acetate and 200 mL distilled water. The organic layer was separated and the aqueous layer was extracted with 100 mL of ethyl acetate. The combined organics were washed successively with distilled water, saturated sodium bicarbonate solution, brine and dried over magnesium sulfate. The solvent was evaporated under vacuum to obtain an orange gum (5.62 g) which was triturated with penme to provide the title compound (4.50 g, 78%) as an off-white solid, m.p. 63°-64° C.

Analalysis calculated for $C_{12}H_{12}N_4O$: C, 63.15; H, 5.30; N, 24.55; Found: C, 63.57; H, 5.27; N, 24.75.

D. 4-Amino-6-cyano-3,4-dihydro-2,2-dimethyl-2H-1-benzopyran

A solution of 4-azido-6-cyano-3,4-dihydro-2,2-dimethyl-2H-1-benzopyran (2.00 g, 8.77 mmol), title C compound, in absolute ethanol (50 mL) was treated with 10% palladium on charcoal (0.25 g) and stirred under hydrogen for 90 minutes at room temperature. The catalyst was filtered off and the filtrate was acidified to pH 1-2 with concentrated HCl (0.85 mL) and concentrated under vacuum to a white solid. The residue was dissolved in 100 mL distilled water and extracted with ethyl acetate (discarded). The aqueous layer was adjusted to pH 11-12 with 50% sodium hydroxide solution and extracted with ethyl acetate. The extracts were washed with brine and dried over magnesium sulfate. The solvent was evaporated under vacuum to provide the title compound (1.542 g, 87%) as a yellow oil which solidified upon standing. The product was used in the next step without further purification.

E. [4R(R*)]-N-(6-cyano-3,4-dihydro-2,2-dimethyl-2H-1-benzopyran-4-yl)-a-hydroxybenzeneacetamide and [4S(S*)]-N-(6-cyano-3,4-dihydro-2,2-dimethyl-2H-1-benzopyran-4-yl)-a-hydroxybenzeneacetamide To a solution of R-(−)-mandelic acid (22.1 g, 0.14 mole) and 1-hydroxy-benzotriazole hydrate (19.6 g, 0.14 mole) cooled to 0° C. was added successively N-methylmorpholine (16.2 g, 0.16 mole), 4-amino-6-cyano-3,4-dihydro-2,2-dimethyl-2H-1-benzopyran (29.4 g, 0.14 mole, title D compound) and 1-(3-dimethylaminopropyl)-2-ethylcarbodiimide hydrochloride (27.9 g, 0.14 mole). The reaction mixture was stirred 0.5 hours at 0° C. and two hours at room temperature. The solvent was recovered under vacuum and the residue was partitioned between 5% aqueous HCl and ethyl acetate. The organic fraction was washed with saturated sodium bicarbonate solution, saturated sodium chloride solution. dried over magnesium sulfate and evaporated in vacuo to obtain 52 g of a yellow gum. The crude diastereomeric mixture was chromatographed on silica eluting with 1:1 hexane/ethyl acetate to obtain [4R(R*)]-N-(6-cyano-3,4-dihydro-2,2-dimethyl-2H-1-benzopyran-4-yl)-α-hydroxybenzeneacetamide (23.2 g, 47.7%, m.p.=120°-121° C. $[a]^D{}_{25}=-39.5°$ (c=1.058, $CHCl_3$). From the column was also recovered [4S(S*)]-N-(6-cyano-3,4-dihydro-2,2-dimethyl-2H-1-benzopyran-4-yl)-α-hydroxybenzeneacetamide (19.8 g, 40.6%), m.p. 135°-136° C. $[a]^D{}_{25}=-60.8°$ (c=0.938, $CHCl_3$).

F. (R)-4-amino-6-cyano-3,4-dihydroxy-2,2-dimethyl-2H-1-benzopyran and (S)-4-amino-6-cyano-3,4-dihydroxy-2,2-dimethyl-2H-1-benzopyran A solution of [4R(R*)]-N-(6-cyano-3,4-dihydro-2,2-dimethyl-2H-1-benzopyran-4-yl)-α-hydroxybenzeneacetamide, title E compound (22.3 g, 66.2) in a mixture of dioxane (195 mL) and 1.5M $H_2SO_4$ (140 mL) was heated at 75°-85° C. for five days. The reaction mixture was concentrated under vacuum and the concentrate was partitioned between distilled water and ethyl acetate. The aqueous phase was washed with ethyl acetate, made basic (pH>12) with 50% NaOH solution and extracted with diethyl ether. The ether extracts were washed with saturated NaCl solution. dried over $Na_2SO_4$ and evaporated in vacuo to obtain 9.58 g (72%) of the title compound as a yellow oil which crystallized on standing. $[\alpha]^D{}_{25}= -95.8°$ (c=0.976, CHCl$_3$). Using the same procedure, (S)-4-amino-6-cyano-3,4-dihydroxy-2,2-dimethyl-2H-1-benzopyran was obtained from [4S(S*)]-N-(6-cyano-3,4-dihydro-2,2-dimethyl-2H-1-benzopyran-4-yl)-a-hydroxybenzeneacetamide (title E compound), as a colorless oil which solidified on standing. $[\alpha]^D{}_{25} = +95.4°$ (c=0.982, CHCl$_3$).

G. (4S)-N''-Cyano-N-(6-cyano-3,4-dihydro-2,2-dimethyl-2H-1-benzopyran-4-yl)-N'-(2,3-dihydro-1H-inden-5-yl)guanidine The solution of N-cyano-N'-[4-indanenyl]thiourea 1 (1.2 g, 6.0 mmol), compound of example 2, part A, and (4S)-4-amino-3,4-dihydro-2,2-dimethyl-2H-1-benzopyran-6-carbonitrile 2 (1.0 g, 5.0 mmol) (title F compound) in dimethylformamide (3 mL) under argon was treated with 1-(3-dimethyl-aminopropyl)-2-ethylcarbodiimide hydrochloride (1.4 g, 7.5 mmol). The reaction was stirred at room temperature for two hours and then partitioned between pH 4 buffer and ethyl acetate. The aqueous phase was reextracted with ethyl acetate and the combined extracts were washed with water (4×200 mL), sodium bicarbonate and brine. After drying over anhydrous magnesium sulfate, the solvent was evaporated and the residue was purified by flash chromatography eluting with a mixture of ethyl acetated/hexanes (1:1) to yield 3 (1.4 g, 73 %). The solid was recrystallized from ethyl ether-hexanes to give the title compound, m.p. 138°-140° C. (foaming, started @ 125°). $[\alpha]_D= +113.9°$ (c=0.9, MeOH).

Analalysis calculated for C$_{23}$H$_{23}$N$_5$O$_1$: C, 71.67: H, 6.01; N, 18.17; Found: C, 71,83; H, 6.31; N, 17.75.

EXAMPLE 10

(3S-trans)-N'''-Cyano-N-(6-cyano-3,4-dihydro-3-hydroxy-2,2-dimethyl-2H-1-benzopyran-4-yl)-N'-[2,3-dihydro-2-(phenylmethyl)-1H-isoindol-5-yl]guanidine A. 2,3-Dihydro-5-nitro-2-(phenylmethyl)-1H-isoindole The title compound was prepared according to the procedure described by T. Yatsunami et at., U.S. Pat. No. 5,026,856, 1991.

B. 5-Amino-2,3-dihydro-2-(phenylmethyl)-1H-isoindole

A suspension of title A compound (2.0 g, 7.8 mmol) in ethanol (50 mL) was treated with stannous chloride hydrate (8.8 g, 38.0 mmol) at room temperature and the reaction mixture was stirred for four hours. The reaction mixture was concentrated in vacuo, basified with saturated potassium carbonate solution, diluted with ethyl acetate (200 mL) and filtered through celite. The two layers were separated and aqueous layer was extracted with ethyl acetate one more time. The combined extracts were washed with brine (100 mL), dried over anhydrous magnesium sulfate and evaporated. The residue was triturated with isopropyl ether to give the title compound (1.3 g, 74%) as a brown solid. m.p. 110°-115° C.

C. 5-[[[(Phenyl)oxy]thiocarbonyl]amino]-2,3-dihydro-2-(phenylmethyl)-1H-isoindole To a solution of title B compound (1.0 g, 4.4 mmol) in dimethylformamide (5 mL) at 0° C. under argon was added pyridine (0.4 mL, 4.4 mmol) followed by phenylthionochloroformate (0.76 g, 4.4 mmol). The reaction mixture was allowed to stir at room temperature for four hours and then poured into water (100 mL). It was extracted with ethyl acetate (2×200 mL) and washed with water (3×100 mL). After drying over anhydrous magnesium sulfate, the solvent was evaporated to give the title compound (1.6 g, 99% ) as an oil which was used for the next step without purification.

D. (3S-trans)-N''-Cyano-N-(6-cyano-3,4-dihydro-3-hydroxy-2,2-dimethyl-2H-1-benzopyran-4-yl)-N'-[2,3-dihydro-2-(phenylmethyl)-1H-isoindol-5-yl]thiourea A solution of (trans)-4-amino-3,4-dihydro-3-hydroxy-2,2-dimethyl-2H-1-benzopyran-6-carbonitrile, methanesulfonic acid salt (1.4 g, 4.5 mmol, compound of example 1, part B) in dimethylformamide (5 mL) under argon was treated with title C compound (1.6 g, 4.5 mmol) and triethylamine (0.6 ml, 4.5 mmol). The reaction mixture was heated at 80° C. for 16 hours, poured into water ( 100 mL) and extracted with ethyl acetate. The combined extracts were washed with water (3×100 mL) and dried over anhydrous magnesium sulfate. The residue, after evaporation of the solvent, was purified by flash chromatography on silica gel eluting with a mixture of ethyl acetate-hexanes (1:1) to yield the title compound (1.1 g, 51%) as an oil.

E. (3aS-trans)-3a,4,9b-trihydro-4,4-dimethyl-2-[5-[2,3-dihydro-2-(phenylmethyl)-1H-isoindol-5-yl]amino]-2H[1]benzopyrano-[4,3-d]-oxazole-8-carbonitrile A mixture of title D compound (1.1 g, 2.3 mmol) and 1-(3-dimethyl-aminopropyl)-2-ethylcarbodiimide hydrochloride (1.3 g, 6.8 mmol) in ethyl acetate (5 mL) was heated at 70° C. for 16 hours. The reaction mixture was diluted with ethyl acetate (200 mL) and washed with water (100 mL). After drying over anhydrous magnesium sulfate, the solvent was evaporated in vacuo to give the title compound as an oil, which was used for the next step without purification.

F. (3S-trans)-N''-Cyano-N-(6-cyano-3,4-dihydro-3-hydroxy-2,2-dimethyl-2H-1-benzopyran-4-yl)-N'-[2,3-dihydro-2-(phenylmethyl)-1H-isoindol-5-yl]guanidine A solution of title E compound (1.0 g, 2.2 mmol) in isopropanol (5 mL) was treated with cyanamide (0.28 g, 6.6 mmol) and triethylamine (0.9 mL, 6.6 mmol). The reaction mixture was heated at 90° for 20 hours and concentrated in vacuo. The residue was diluted with ethyl acetate (200 mL) and washed with water (100 mL). After drying over anhydrous magnesium sulfate, the solvent was evaporated and the residue was purified by flash chromatography eluting with a mixture of hexanes-ethyl acetate (3:7) to give a colorless solid (0.5 g, 46%). It was triturated with isopropyl ether to give the title product as a colorless solid, m.p. 203°-210° C. (foaming, started @ 156°). $[\alpha_D]= -32.9°$ (c=0.592, DMF).

Analysis calculated for C$_{29}$H$_{28}$N$_6$O$_2$.0.52 H$_2$O: C, 69.40; H, 5.83; N, 16.79; Found: C, 69.35; H, 5.96; N, 16.79.

EXAMPLE 11

[3S-[3a,4b(S*)]]-N'''-Cyano-N-(6-cyano-3,4-dihydro-3-hydroxy-2,2-dimethyl-2H-1-benzopyran-4-yl)-N'-[2,3-dihydro-2-(1-phenylmethyl)-1H-isoindol-5-yl]guanidine A. 5-Amino-2-(1-phenylmethyl)-2,3-dihydroisoindole The title compound was prepared by the same procedure as described for the synthesis of 5-amino-2-benzyl-2,3-isoindolinc (example 10, part B) and was obtained as a brown solid, m.p. 136°-138° C.

B. [3S-[3a,4b(S*)]]-N'''-Cyano-N-(6-cyano-3,4-dihydro-3-hydroxy-2,2-dimethyl-2H-1-benzopyran-4-yl)-N'-[2,3-dihydro-2-(1-phenylmethyl)-1H-isoindol-5-yl]guanidine The title compound was prepared from 5-amino-2-(1-phenylmethyl)-2,3-dihydroisoindole (title A compound) by the same procedure as described in Example 10 to give a colorless solid, m.p. 155°–160° C. (foaming, started @ 148°). $[\alpha_D] = -42.38°$ (c=0.64, DMF).

Analysis calculated for $C_{30}H_{30}N_6O_2 \cdot 0.44\ H_2O$: C, 70.04; H, 6.05; N, 16.34; Found: C, 70.04; H, 5.91; N, 16.21.

EXAMPLE 12

(3S-trans)-N''-cyano-N-(6-cyano-3,4-dihydro-3-hydroxy-2,2-dimethyl-2H-1-benzopyran-4-yl)-N'-[2,3-dihydro-2-(1-phenyl-1H-isoindol-5-yl]guanidine A. 5-Amino-2-phenyl-2,3-dihydroisoindole The title compound was prepared by the same procedure as described for the synthesis of 5-amino-2-benzyl-isoindoline (example 10, part B).

B. (3S-trans)-N''-Cyano-N-(6-cyano-3,4-dihydro-3-hydroxy-2,2-dimethyl-2H-1-benzopyran-4-yl)-N'-[2,3-dihydro-2-(1-phenyl-1H-isoindol)-5-yl]guanidine Using the procedure described in Example 10, the title compound was prepared from title A compound and the product was purified by flash chromatography eluting with a mixture of hexanes/ethyl acetate (4:6). The residue was crystallized from isopropanol-ethyl ether to give a colorless solid, m.p. 186°–189° C. (foaming, started @ 176°). $[\alpha_D]^{25} = -19.5°$ (c=0.308, DMF).

Analysis calculated for $C_{28}H_{26}N_6O_2 \cdot 0.43\ H_2O$: C, 69.16; H, 5.57; N, 17.28; Found: C, 69.29; H, 5.27; N, 17.15.

EXAMPLE 13

(3S-trans)-N''-Cyano-N-(6-cyano-3,4-dihydro-3-hydroxy-2,2-dimethyl-2H-1-benzopyran-4-yl)-N'-[3-(3-methyl-1,2,4-oxadiazol-5-yl)phenyl]guanidine The title compound was prepared by the same procedure as described in Example 10 to give a colorless solid, m.p. 186°–190° C. $[\alpha]_D = -13.0°$ (c=0.56, DMSO).

Analysis calculated for $C_{23}H_{21}N_7O_3 \cdot 0.06\ C_6H_{14} \cdot 0.2\ H_2O$: C, 60.55; H, 5.11; N, 21.16; Found: C, 60.54; H, 4.91; N, 20.82. MS (M+H)+ at 444, M.W. 443.

EXAMPLE 14

(3S-trans)-N''-Cyano-N-(6-cyano-3,4-dihydro-3-hydroxy-2,2-dimethyl-2H-1-benzopyran-4-yl)-N'-[3-(2-oxazolyl)phenyl]guanidine The title compound was prepared by the same procedure as described in Example 10 to yield a colorless powder, m.p. 156°–161° C.

Analysis calculated for $C_{23}H_{20}N_6O_3 \cdot 0.37\ H_2O$: C, 63.49; H, 4.80; N, 19.31; Found: C, 63.87; H, 4.77; N, 18.93. MS (M+H)+ at 429, M.W. 428. $[\alpha]_D = -3.3°$ (c=0.77, DMSO).

EXAMPLE 15

(3S-trans)-N''-Cyano-N-(6-cyano-3,4-dihydro-3-hydroxy-2,2-dimethyl-2H-1-benzopyran-4-yl)-N'-[3-(3-methyl5-isoxazolyl)phenyl]guanidine The title compound was prepared by the same procedure as described in Example 10 to give a colorless powder, m.p. 175°–178° C.

Analysis calculated for $C_{24}H_{22}N_6O_3 \cdot 0.54\ H_2O$: C, 63.75; H, 5.14; N, 18.59; Found: C, 64.15; H, 4.86; N, 18.19. MS (M+H)+ at 443, M.W. 442. $[\alpha]_D = +21.4°$ (c=0.76, MeOH).

EXAMPLE 16

(3S-trans)-N''-Cyano-N-(6-cyano-3,4-dihydro-3-hydroxy-2,2-dimethyl-2H-1-benzopyran-4-yl)-N'-[3-(1,3-dimethyl-1H-pyrazol-5-yl)phenyl]-guanidine The title compound was prepared by the same procedure as described in Example 10 to provide a colorless solid, m.p. 157°–163° C.

Analysis calculated for $C_{25}H_{25}N_7O_2 \cdot 0.30\ C_4H_8O_2 \cdot 0.17\ H_2O$: C, 64.88; H, 5.76; N, 20.22; Found: C, 64.89; H, 5.72; N, 20.25. MS (M+H)+ at 456, M.W. 455. $[\alpha]_D = +9.9°$ (c=0.79, MeOH).

EXAMPLE 17

(3S-trans)-N''-Cyano-N-(6-cyano-3,4-dihydro-3-hydroxy-2,2-dimethyl-2H-1-benzopyran-4-yl)-N'-[3-(1,5-dimethyl-1H-pyrazol-3-yl)phenyl]guanidine The title compound was prepared by the same procedure as described in Example 10 to give an off-white powder, m.p. 153°–159° C.

Analysis calculated for $C_{25}H_{25}N_7O_2 \cdot 0.32\ C_4H_8O_2 \cdot 0.11\ H_2O$: C, 64.99; H, 5.76; N, 20.19: Found: C, 64.98; H, 5.69: N, 20.05. MS (M+H)+ at 456, M.W. 455. $[\alpha]_D = +12.6°$ (c=0.69, MeOH).

EXAMPLE 18

(3S-trans)-N''-Cyano-N-(6-cyano-3,4-dihydro-3-hydroxy-2,2-dimethyl-2H-1-benzopyran-4-yl)-N'-[4-[methyl(phenylmethyl)amino]phenyl]guanidine The title compound was prepared by the same procedure as described in Example 10 to give a yellow powder, m.p. 182°–184° C.

Analysis calculated for $C_{29}H_{30}N_6O_2 \cdot 0.18\ H_2O$: C, 69.97; H, 6.15; N, 16.88; Found: C, 70.22: H, 6.13: N, 16.63. MS (M+H)+ at 495, M.W. 494. $[\alpha]_D = -13.8°$ (c=0.71, MeOH).

EXAMPLE 19

(3S-trans)-N''-Cyano-N-(6-cyano-3,4-dihydro-3-hydroxy-2,2-dimethyl-2H-1-benzopyran-4-yl)-N'-[2-[methyl(phenylmethyl)amino]phenyl]guanidine The title compound was prepared by the same procedure as described in Example 10 to give a colorless powder, m.p. 118°–121° C.

Analysis calculated for $C_{29}H_{30}N_6O_2 \cdot 0.07\ Et_2O \cdot 0.08\ H_2O$: C, 70.16; H, 6.21; N, 16.77; Found: C, 70.16; H, 6.30; N, 16.33. MS (M+H)+ at 495, M.W. 494. $[\alpha]_D = -108.8°$ (c=0.96, MeOH).

EXAMPLE 20

(3S-trans)-N''-Cyano-N-(6-cyano-3,4-dihydro-3-hydroxy-2,2-dimethyl-2H-1-benzopyran-4-yl)-N'-(2-biphenyl)guanidine The title compound was prepared by the same procedure as described in Example 10 to give a colorless solid, m.p. 151°–154° C.

Analysis calculated for $C_{26}H_{23}N_5O_2 \cdot 0.94\ H_2O$: C, 68.72; H, 5.52; N, 15.41; Found: C, 69.02; H, 5.25; N, 15.11. MS (M+H)+ at 438, M.W. 437. $[\alpha]_D = +7.9°$ (c=0.70, MeOH).

EXAMPLE 21

(3S-trans)-5-[[[(6-Cyano-3,4-dihydro-3-hydroxy-2,2-dimethyl-2H-1-benzopyran-4-yl)amino]carbonyl]amino]-1,3-dihydro-2H-isoindol-2carboxylic acid, 2,2,2-trichloroethyl ester A. 5-Nitro-2,3-dihydroisoindol-2-carboxylic acid, 2,2,2-trichloroethyl ester A solution of rifle 10 A compound (10.0 g, 50 mmol, compound of example 10, pan A) in acetonitrile (30 mL) was treated with trichloroethyl chloroformate (10.0 g, 50 mmol) and the reaction mixture was heated at 80° C. for three hours. It was then concentrated in vacuo and purified by flash chromatography on silica gel (30% ethyl acetate in hexanes) to yield an offwhite solid (7 g, 41%) which was triturated with diethyl ether to provide a colorless solid, m.p. 115°–116° C.

Analysis calculated for $C_{11}H_1Cl_3N_2O_4$: C, 38.68; H, 3.25; N, 8.20; Cl, 31.14; Found: C, 39.24; H, 2.84; N, 8.33; Cl, 31.01.

B. 5-Amino-1,3-dihydro-isoindol-2-carboxylic acid, 2,2,2-trichloroethyl ester

A solution of 5-nitroisoindol-2-carboxylic acid, 2,2,2-trichloroethyl ester (2.0 g, 5.9 mmol, title A compound) in ethyl acetate (20 mL) was treated with stannous chloride hydrate (6.6 g, 29.3 mmol) and the reaction mixture was heated under reflux for three hours. It was basified with saturated potassium carbonate solution, diluted with ethyl acetate (200 mL) and filtered through a celite pad. The layers were separated and the aqueous layer was extracted with ethyl acetate. The combined organic extracts were washed with brine (100 mL), dried over anhydrous magnesium sulfate and evaporated in vacuo to give the title compound (1.6 g, 88.6%) as an oil.

C. (3S-trans)-5-[[[(6-Cyano-3,4-dihydro-3-hydroxy-2,2-dimethyl-2H-1-benzopyran-4-yl)amino]carbonyl]amino]1,3-dihydro-2H-isoidindol-2-carboxylic acid, 2,2,2-trichloroethyl ester The title compound was prepared from (trans)-4-amino-3,4-dihydro-3-hydroxy-2,2-dimethyl-2H-1-benzopyran-6-carbonitrile (compound of example 1, pan B) and title B compound (1.5 g, 4.5 mmol) by the procedure described in Example 8 to give a colorless solid, m.p. 201°–203° C. (foaming, started @ 155°). $[\alpha_D]^{25} = -44.4°$ (c=0.475, MeOH).

Analysis calculated for $C_{24}H_{23}N_4O_5Cl_3.05\ H_2O$: C, 51.97; H, 4.20; N, 10.10; Cl, 19.17; Found: C, 52.19; H, 4.25; N, 9.88; Cl, 19.47.

EXAMPLE 22

(3S-trans)-N-(6-cyano-3,4-dihydro-3-hydroxy-2,2-dimethyl-2H-1-benzopyran-4-yl)-N'-(2,3-dihydro-2-methyl-1H-isoindol-5-yl)urea A. 2-methyl-5-amino-1,3-dihydroisoindole To a suspension of lithium aluminium hydride (0.36 g, 9.7 mmol) in anhydrous tetrahydrofuran (10 mL) at 0° C. was slowly added a solution of title 21 B compound (1.0 g, 3.2 mmol) in trahydrofuran (5 mL). After the addition was finished, the cooling bath was removed and the reaction mixture was stirred at room temperature for two hours. It was cooled to 0° C. and excess reagent was decomposed with water. The reaction mixture was diluted with diethyl ether and filtered through. The layers were separated and the aqueous layer was reextracted with chloroform (150 mL). The combined organic extracts were washed with brine (100 mL), dried over anhydrous magnesium sulfate and evaporated in vacuo to give the title product (0.4 g, 83%) as an oil.

B. (3S-trans)-N-(6-cyano-3,4-dihydro-3-hydroxy-2,2-dimethyl-2H-1-benzopyran-4-yl)-N'-(2,3-dihydro-2-methyl-1H-isoindol-5-yl)urea The title compound was prepared from (trans)-4-amino-3,4-dihydro-3-hydroxy-2,2-dimethyl-2H- 1-benzopyran-6-carbonitrile (0.42 g, 1.3 mmol, compound of example 1, part B) and title A compound by the procedure described in Example 8 to give a colorless solid, m.p. 220°–222° C. (foaming, started @ 155°). $[\alpha_D] = -12.8°$ (c=0.525, DMF).

Analysis calculated for $C_{22}H_{24}N_4O_3.53\ H_2O$: C, 65.74; H, 6.28; N, 13.94; Found: C, 66.19; H, 6.32; N, 13.49.

EXAMPLE 23

(3S-trans)-N-(6-cyano-3,4-dihydro-3-hydroxy-2,2-dimethyl-2H-1-benzopyran-4-yl)-N'-(2,3-dihydro-1H-isoindol-5-yl)urea A solution of (3S-trans)-N-(6-cyano-3,4-dihydro-3-hydroxy-2,2-dimethyl-2H-1-benzopyran-4-yl)-N'-(2,3-dihydro-2-methyl-1H-isoindol-5-yl)urea (1.0 g, 1.8 mmol, compound of example 19) in acetic acid (4 mL) was treated with zinc dust (0.35 g, 5.4 mmol) under argon and heated at 80° C. for 16 hours. Additional amount (0.4 g) of zinc dust was added and the reaction mixture was heated for eight hours. It was cooled to room temperature, diluted with chloroform (100 mL) and filtered. The solvent was evaporated in vacuo and the residue was acidified with 10% hydrochloric acid (10 mL). It was then extracted with ethyl acetate and the organic extract was discarded. The acid layer was made basic (pH~11) with 10% sodium hydroxide solution, saturated with salt and extracted with chloroform (3×100 mL). The aqueous layer was filtered and the filtrate was concentrated in vacuo. The residue was diluted with 40% aqueous isopropanol. The precipitate was faltered and dried to yield the title compound (0.2 g) as a colorless solid, m.p. 215°–217° C. $[\alpha_D]^{25} = -13.9°$ (c=0.42, DMF).

Analysis calculated for $C_{21}H_{22}N_4O_3.0.18\ C_3H_8O$: C, 66.47; H, 6.07; N, 14.39. Found: C, 66.36; H, 5.73: N, 13.98.

EXAMPLE 24

(3S-trans)-N-(6-Cyano-3,4-dihydro-3-hydroxy-2,2-dimethyl-2H-1-benzopyran-4-yl)-N'-[3-(3-methyl-5-isoxazolyl)phenyl]urea The title compound was prepared by the same procedure as described in Example 8 to give a colorless solid, m.p. 140°–148° C. (foam).

Analysis calculated for $C_{23}H_{22}N_4O_4.0.25\ H_2O$: C, 65.32; H, 5.36; N, 13.25; Found: C, 65.70; H, 5.51; N, 12.87. MS (M+H)+ at 419, M.W. 418. $[\alpha]_D = -51.0°$ (c=0.69, MeOH).

EXAMPLE 25

(3S-trans)-N-(6-Cyano-3,4-dihydro-3-hydroxy-2,2-dimethyl-2H-1-benzopyran-4-yl)-N'-[3-(1,3-dimethyl-1H-pyrazol-5-yl)phenyl]urea The title compound was prepared by the same procedure as described in Example 8 to give a colorless solid, m.p. 142°–152° C. (foam).

Analysis calculated for $C_{24}H_{25}N_5O_3.0.38\ H_2O$: C, 65.76; H, 5.92; N, 15.98; Found: C, 66.17; H, 5.89; N, 15.57. MS (M+H)+ at 432, M.W. 431. [α]$_D$= −53.3° (c=0.66, MeOH).

EXAMPLE 26

(3S-trans)-N-(6-Cyano-3,4-dihydro-3-hydroxy-2,2-dimethyl-2H-1-benzopyran-4-yl)-N'-[3-(1,5-dimethyl-1H-pyrazol-3-yl)phenyl]urea The title compound was prepared by the same procedure as described in Example 8 to give a colorless powder, m.p. 120°–130° C. (foam).

Analysis calculated for $C_{24}H_{25}N_5O_3.0.52\ H_2O$: C, 65.38; H, 5.95; N, 15.89; Found: C, 65.68; H, 6.07; N, 15.59. MS (M+H)+ at 432, M.W. 431. [α]$_D$= −54.5° (c=0.29, MeOH).

EXAMPLE 27

(3S-trans)-N-(6-Cyano-3,4-dihydro-3-hydroxy-2,2-dimethyl-2H-1-benzopyran-4-yl)-N'-[3-(5-methyl-3-isoxazolyl)phenyl]urea The title compound was prepared by the same procedure as described in Example 8 to give a colorless powder, m.p. 110°–120° C. (foam).

Analysis calculated for $C_{23}H_{22}N_4O_4.0.1\ C_4H_8O_2.0.45\ H_2O$: C, 64.56; H, 5.49; N, 12.87; Found: C, 64.88; H, 5.55; N, 12.55. MS (M+H)+ at 419, M.W. 418. [α]$_D$= −41.9° (c=0.47, MeOH).

EXAMPLE 28

(3S-trans)-N-(6-Cyano-3,4-dihydro-3-hydroxy-2,2-dimeth-yl-2H-1-benzopyran-4-yl)-N'-[4-[[methyl(-phenylmethyl)amino]methyl]phenyl]urea, monohydrochloride The title compound was prepared by the same procedure as described in Example 8 and isolated as the hydrochloride salt (from ether). m.p. 175°–185° C.

Analysis calculated for $C_{28}H_{30}N_4O_3.HCl.0.42\ H_2O$: C, 65.36; H, 6.24; N, 10.89; Cl, 6.89; Found: C, 65.59; H, 6.37: N. 10.66; Cl, 6.88. MS (M+H)+ at 471, M.W. 470. [α]$_D$= −55.2° (c=0.56, MeOH).

EXAMPLE 29

(3 S-trans)-N-(6-Cyano-3,4-dihydro-3-hydroxy-2,2-dimethyl-2H-1-benzopyran-4-yl)-N-[2,3-dihydro-2-(phenylmethyl)-1H-isoindol-5-yl]urea, The title compound was prepared from 5-amino-2,3-dihydro-2-(phenylmethyl)isoindole (title 10B compound) and title title 1B compound by the procedure described in Example 10 to give a colorless solid, m.p. 168°–175° C. (foams at 150° .C). [α]$_D$= −43.3° (c=0.9, MeOH).

Analysis calculated for $C_{28}H_{28}N_4O_3.0.25CHCl_3.2.0\ H_2O$: C, 63.49; H, 6.08; N, 10.48; Found: C, 63.79; H. 5.72; N, 10.73.

EXAMPLE 30

(3S-trans)-N-(6-Cyano-3,4-dihydro-3-hydroxy-2,2-dimethyl-2H-1-benzopyran-4-yl)-N'-[3-[[methyl(-phenylmethyl)amino]methyl]phenyl]urea, monohydrochloride A.
(3S-trans)-4-phenoxycarbonylamino-3,4-dihydro-3-hydroxy-2,2-dimeth-yl-2H-1-benzopyran-6-carbonitrile A mixture of (3S-trans)-4-amino-3,4-dihydro-3-hydroxy-2,2-dimethyl-2H-1-benzopyran-6-carbonitrile, methanesuffonic acid salt (3.18 g, 10.0 mmol, Example 1, title B compound) in aceonitrile (50 mL)/pyridine (5 mL) under argon at 0 ° C. was treated with phenyl chloroformate (1.25 mL, 1.56 g, 10.0 mmol). After three hours, volatiles were removed in vacuo and the residue, dissolved in ethyl acetate, was washed with 10% citric acid, water and brine, dried (anhydrous magnesium sulfate) and concentrated to give 3.65 g of a clear oil. Crystallization from ethyl acetate/hexanes (2:5) gave the title product (2.75 g, 81%), m.p. 154°–155° C.

Analysis calculated for $C_{19}H_{18}N_2O_4$: C, 67.20; H, 5.36; N, 8.25; Found: C, 67.47; H, 5.94; N, 8.23. [α]$_D$= −77.8° (c=0.54, MeOH).

B. (3S-trans)-N-(6-Cyano-3,4-dihydro-3-hydroxy-2,2-dimethyl-2H-1-benzopyran-4-yl )-N'-[3-[[methyl(-phenylmethyl)amino]-methyl]phenyl]urea, monohydrochloride A mixture of title A compound (680 mg, 2.0 mmol) and N-(phenylmethyl)-N-(3-amino(phenyl)methyl)methylamine (460 mg, 2.0 mmol) in 10 mL of DMF was heated at 120° C. for five hours. The mixture was diluted with ethyl acetate and washed with 5% sodium bicarbonate water and brine, dried (anhydrous magnesium sulfate) and concentrated in vacuo to give a foam (1.38 g). Flash chromatography on silica gel (ethyl acetate/hexanes) gave a foam (640 mg, 68%) which was converted to its hydrochloride salt (ethyl acetate/hexanes) to give the title product (620 mg, 90%), m.p. 145°–150° C.

Analysis calculated for $C_{28}H_{30}N_4O_3.HCl.0.16\ H_2O$: C, 65.95; H, 6.19; N, 10.99; Cl, 6.95; Found: C, 66.28; H, 6.41; N, 10.66; Cl, 6.97. [α]$_D$= −60.0° (c=0.46 MeOH).

EXAMPLE 31

(3S-trans)-N-(6-Cyano-3,4-dihydro-3-hydroxy-2,2-dimethyl-2H-1-benzopyran-4-yl)-N'-[2-[[methyl(-phenylmethyl)amino]methyl]phenyl]urea, monohydrochloride The title compound was prepared by the same procedure as described in Example 29 to give a colorless powder, m.p. 165°–169° C.

Analysis calculated for $C_{28}H_{30}N_4O_3.HCl.0.47\ H_2O$: C, 65.25; H, 6.24; N, 10.87; Cl, 6.88; Found: C, 66.27; H, 6.19; N, 10.89; Cl 6.94. MS (M+H)+ at 471, M.W. 470. [α]$_D$= +90.0° (c=0.50 MeOH).

EXAMPLE 32

(3S-trans)-N-(6-Cyano-3,4-dihydro-3-hydroxy-2,2-dimethyl-2H-1-benzopyran-4-yl)-N'-[3-(5-imidazolyl)-phenyl]urea The title compound was prepared by the same procedure as described in Example 29 to give an off-white solid, m.p. 170°–180° C.

Analysis calculated for $C_{22}H_{21}\ N_5O_3.0.38\ H_2O$: C, 64.41; H, 5.35; N, 17.07; Found: C, 64.45; H, 5.45;, N, 17.03. MS, (M+H)+ at 404, M.W. 403. [α]$_D$= +90.0° (c=0.50, MeOH).

EXAMPLE 33

(3S-trans)-N'-(4-Chlorophenyl)-N-(6-cyano-3,4-dihydro-3-hydroxy-2,2-dimethyl-2H-1-benzopyran-4-yl)-N-[2-(dimethylamino)]urea A. (3S-trans)-4-((2-Dimethylamino)ethyl)amino-3,4-dihydro-3-hydroxy-2,2-dimethyl-2H-1-benzopyran-6-carbonitrile The suspension containing the title 1A compound (500 mg, 2.5 mmol) and 2,2-dimethlaminoethyl amine (260 mg of 97%, 2.75 mmol) in ethanol (5.0 mL) and tetrahydrofuran (2.0 mL) was heated at 75° C. for 20 hours. The solvent was evaporated to yield a colorless oil (711 mg, 100%) which was submitted to the next reaction without further purification.

B. (3S-trans)-N'-(4-Chlorophenyl)-N-(6-cyano-3,4-dihydro-3-hydroxy-2,2-dimethyl-2H-1-benzopyran-4-yl)-N-[2-(dimethylamino)]urea The solution containing (3S-trans)-4-(((2,2-dimethyl)amino)ethyl)amino-3,4-dihydro-3-hydroxy-2,2-dimethyl-2H-1-benzopyran-6carbonitrile (711 mg, title A compound) in acetonitrile (5.0 mL) was treated with 4-chlorophenyl isocyanate (383 mg, 2.5 mmol) and the reaction mixture was allowed to stir at room temperature for 16 hours. The solvent was evaporated and the residue was purified by flash chromatography (ethyl acetate) to yield a colorless foam. This material in ether was converted to its hydrochloride salt by treatment with anhydrous hydrochloric acid solution in ether to give the title compound as a colorless powder (800 mg, 66.6%), m.p. 165°-175° C. (shrinks @ 150° C.). $[\alpha]_D = -77.6°$ (c=1, MeOH).

Analysis calculated for $C_{23}H_{27}N_4ClO_3 \cdot HCl \cdot 0.4\, H_2O$: C, 56.77; H, 5.97; N, 11.51; Cl, 14.57; Found: C, 56.84; H, 6.01; N, 11.32; Cl, 14.43.

EXAMPLE 34

(3S-trans)-N'-(4-Chlorophenyl)-N-(6-cyano-3,4-dihydro-3-hydroxy-2,2-dimethyl-2H-1-benzopyran-4-yl)-N-[2-(dimethylamino)ethyl]urea A. 4-Chloro-N-[(2-dimethylamino)ethyl]aniline To an ice cold reaction mixture containing 4-chloroaniline (1.28 g, 10.0 mmol) and 2-dimethylaminoethyl chloride (6 mL of a 2M solution in toluene) in dimethylformamide (5.0 mL) under argon was added sodium hydride (515 mg of 60% dispersion, 13.0 mmol). The cooling bath was removed and the reaction was stirred at room temperature for two hours. The reaction mixture was heated at 65° C. for 16 hours. The reaction mixture was allowed to cool to ambient temperature and carefully diluted with water. It was extracted with ethyl acetate; ethyl acetate extracts were washed with water and dried over magnesium sulfate. The solvent was evaporated to yield a brown oil. This material was combined with another batch of the same product and purified by flash chromatography on silica gel (10% methanol in dichloromethane) to yield the title compound as a yellow oil.

B. (3S-trans)-N'-(4-Chlorophenyl)-N-(6-cyano-3,4-dihydro-3-49hydroxy-2,2-dimethyl-2H-1-benzopyran-4-yl)-N-[2-(dimethylamino)ethyl]urea The reaction mixture containing title A compound (578 mg, 2.89 mmol), and title 29A compound (1.07 g, 3.17 mmol) and 4-dimethylaminopyridine (20 mg, 0.16 mmol) in acetonitrile (10 mL) was heated at 80° C. for 48 hours. The solvent was evaporated and the residue was purified by flash chromatography (7.5% methanol in dichloromethane) to yield a colorless foam (365 mg, 28.5%). This material in isopropanol was converted to its hydrochloride salt by treatment with ethereal hydrochloric acid to give the title compound as an off-white solid (307 mg), m.p. 145°-155° C. with foaming. $[\alpha]_D = +71°$ (c=0.5, MeOH).

Analysis calculated for $C_{23}H_{27}ClN_4O_3 \cdot HCl \cdot 0.63\text{-}H_2O$: C, 56.29; H, 6.01; N, 11.41; Cl, 14.45; Found: C, 56.62; H, 6.06; N, 11.09; Cl, 14.71.

What is claimed is:

1. A compound of the formula I

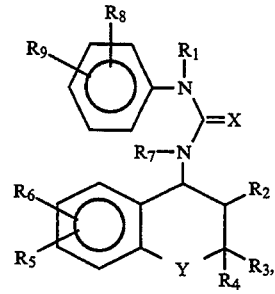

or pharmaceutically acceptable salts thereof wherein,
X is oxygen, sulfur or —NCN;
Y is oxygen,
$R_1$ and $R_7$ are independently hydrogen, alkyl, arylalkyl, -(alkyl)amino or -(alkyl)substituted amino;
$R_2$ is hydrogen, hydroxy or

$R_3$ and $R_4$ are each independently hydrogen, alkyl or arylalkyl; or, $R_3$ and $R_4$ taken together with the carbon atom to which they are attached form a 5- to 7-membered carbocyclic ring;
$R_5$ is hydrogen, alkyl, haloalkyl, alkenyl, alkynyl, cycloalkyl, arylalkyl, cycloalkylalkyl, —CN, —NO$_2$, —COR$^a$, —COOR$^a$, —CONHR$^a$, —CON(R$^a$)$_2$, —CF$_3$, —S—alkyl, —SOalkyl, —SO$_2$alkyl,

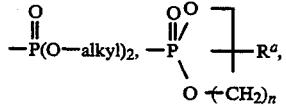

halogen, amino, substituted amino, —O-alkyl, —OCF$_3$, —OCH$_2$CF$_3$, —OCOalkyl, —OCONR$^a$alkyl, —NR$^a$COalkyl, —NR$^a$COOalkyl or —N(R$^a$)CON(R$^a$)$_2$ wherein R$^a$ is hydrogen, alkyl, aryl, arylalkyl, cycloalkyl, (cycloalkyl)alkyl or haloalkyl;
$R_6$ is hydrogen, alkyl, halo, —OH, —O-allkyl, amino, substituted amino, —O-alkyl, —O-haloalkyl, —O-COalkyl, —OCONR$^a$alkyl, —NR$^a$COalkyl, —N-R$^a$COOalkyl or —NR$^a$CON(R$^a$)$_2$;
$R_8$ is hydrogen, alkyl, —O-alkyl, —S-alkyl, halo or nitro;
$R_9$ is aryl, heterocyclo, -(alkyl)amino or-(alkyl)substituted amino; or
$R_8$ and $R_9$ and the atoms to which they are attached complete a 5- to 7- membered ring which may contain one to three hetero atoms (O, S, NR$^b$), CO, SO, SO$_2$; wherein R$^b$ is hydrogen, alkyl, aryl, arylalkyl, COalkyl, alkyl, CO-haloalkyl, CO-substituted amino; or
$R_1$ and $R_7$, $R_7$ and $R_8$ or $R_1$ and $R_8$ taken together with the atoms to which they are attached form a 5- to 7- membered ring; and n is 1, 2 or 3.

2. The compound of claim 1 wherein
$R_1$ is hydrogen or -(alkyl)amino or -(alkyl)substituted amino:
$R_2$ is hydrogen or hydroxy;
$R_3$ and $R_4$ are each alkyl;
$R_5$ is an electron withdrawing group;
$R_6$ is hydrogen, alkyl or O-alkyl;
$R_7$ is hydrogen;
$R_8$ is heterocyclo, -(alkyl)amino, -(alkyl)substituted amino or aryl;
$R_9$ is hydrogen; or
$R_8$ and $R_9$ form a 5- to 6-membered ring.

3. The compound of claim 1 wherein
$R_1$ is hydrogen or $CH_2CH_2NMe_2$;
$R_2$ is trans-hydroxy;
$R_3$ and $R_4$ are each methyl;
$R_5$ is —CN or —$NO_2$;
$R_6$ is hydrogen;
$R_7$ is hydrogen or $CH_2CH_2NMe_2$;
$R_8$ is oxazole, tetrazole, oxadiazole, methyloxadiazole, isoxazole, dimethylpyrazole or $CH_2N(Me)CH_2Ph$;
$R_9$ is hydrogen; or
$R_8$ and $R_9$ and the atoms to which they are attached complete an indane ring which may contain one to three hetero atoms.

4. A compound of claim 1 which is (3S-trans)-3-(6-cyano-3,4-dihydro-3-hydroxy-2,2-dimethyl-2H-1-benzopyran-4-yl)-N'-(2,3-dihydro-1-H-inden-5-yl)urea.

5. A compound of claim 1 which is (3S-trans)-N''-cyano-N-(6-cyano-3,4-dihydro-3-hydroxy-2,2-dimethyl-2H-1-benzopyran-4-yl)-N'-[4-(2,3-dihydro-1H-inden-5-yl)]guanidine.

6. A compound of claim 1 which is (3S-trans)-N-(6-cyano-3,4-dihydro-3-hydroxy-2,2-dimethyl-2H-benzopyran-4-yl)-N'-[4-(1H-tetrazol-5-yl)phenyl]urea.

7. A compound of claim 1 which is (3S-trans)-N-(6-cyano-3,4-dihydro-3-hydroxy-2,2-dimethyl-2H-1-benzopyran-4-yl)-N'-[3-(1H-tetrazol-5-yl)phenyl]urea.

8. A compound of claim 1 which is (3S-trans)-N-(6-cyano-3,4-dihydro-3-hydroxy-2,2-dimethyl-2H-1-benzopyran-4-yl)-N'-[3-(1,2,4-oxadiazol-5-yl)phenyl]urea.

9. A compound of claim 1 which is (3S-trans)-N-(6-cyano-3,4-dihydro-3-hydroxy-2,2-dimethyl-2H-1-benzopyran-4-yl)-N'-[4-(1,2,4-oxadiazol-5-yl)phenyl]urea.

10. A compound of claim 1 which is (3S-trans)-N-(6-cyano-3,4-dihydro-3-hydroxy-2,2-dimethyl-2H-1-benzopyran-4-yl)-N'-[3-[3-methyl-(1,2,4-oxadia-zol-5-yl)]phenyl]urea.

11. A compound of claim 1 which is (3S-trans)-N-(6-cyano-3,4-dihydro-3-hydroxy-2,2-dimethyl-2H-1-benzopyran-4-yl)-N'-[3-(1,3-oxazol-5-yl)]phenylurea.

12. A compound of claim 1 which is N''-cyano-N-(6-cyano-3,4-dihydro-2,2-dimethyl-2H-1-benzopyran-4-yl)-N'-(2,3-dihydro-1H-inden-5-yl)guanidine.

13. A compound of claim 1 which is (3S-trans)-N''-cyano-N-(6-cyano-3,4-dihydro-3-hydroxy-2,2-dimethyl-2H-1-benzopyran-4-yl)-N'-[2,3-dihydro-2-(phenylmethyl )-1H-isoindol-5- yl]guanidine.

14. A compound of claim 1 which is [3S-[3a,4b(S*)]]-N''-cyano-N-(6-cyano-3,4-dihydro-3-hydroxy-2,2-dimethyl-2H-1-benzopyran-4-yl)-N'-[2,3-dihydro-2-(1-phenylmethyl)-1H-isoindol-5-yl]guanidine.

15. A compound of claim 1 which is (3S-trans)-N''-cyano-N-(6-cyano-3,4-dihydro-3-hydroxy-2,2-dimethyl-2H-1-benzopyran-4-yl)-N'-[2,3-dihydro2-(1-phenyl-1H-isoindol-5-yl]guanidine.

16. A compound of claim 1 which is (3S-trans)-N''-cyano-N-(6-cyano-3,4-dihydro-3-hydroxy-2,2-dimethyl-2H-1-benzopyran-4-yl)-N'-[3-(3-methyl-1,2,4-oxadiazol-5-yl)phenyl]guanidine.

17. A compound of claim 1 which is (3S-trans)-N''-cyano-N-(6-cyano-3,4-dihydro-3-hydroxy-2,2-dimethyl-2H-1-benzopyran-4-yl)-N'-[3-(2-oxazolyl)phenyl]guanidine.

18. A compound of claim 1 which is (3S-trans)-N''-cyano-N-(6-cyano-3,4-dihydro-3-hydroxy-2,2-dimethyl-2H-1-benzopyran-4-yl)-N'-[3-(3-methyl-5-isoxazolyl)phenyl]guanidine.

19. A compound of claim 1 which is (3S-trans)-N''-cyano-N-(6-cyano-3,4-dihydro-3-hydroxy-2,2-dimethyl-2H-1-benzopyran-4-yl)-N'-[3-(1,3-dimethyl-1H-pyrazol-5-yl)phenyl ]guanidine.

20. A compound of claim 1 which is (3S-trans)-N''-cyano-N-(6-cyano-3,4-dihydro-3-hydroxy-2,2-dimethyl-2H-1-benzopyran-4-yl)-N'-[3-(1,5-dimethyl-1H-pyrazol-3-yl)phenyl]guanidine.

21. A compound of claim 1 which is (3S-trans)-N''-cyano-N-(6-cyano-3,4-dihydro-3-hydroxy-2,2-dimethyl-2H-1-benzopyran-4-yl)-N'-[4-[methyl(phenylmethyl)amino phenyl]guanidine.

22. A compound of claim 1 which is (3S-trans)-N''-cyano-N-(6-cyano-3,4-dihydro-3-hydroxy-2,2-dimethyl-2H-1-benzopyran-4-yl)-N'-[2-[methyl(phenylmethyl)amino]phenyl]guanidine.

23. A compound of claim 1 which is (3S-trans)-N''-cyano-N-(6-cyano-3,4-dihydro-3-hydroxy-2,2-dimethyl-2H-1-benzopyran-4-yl)-N'-(2-biphenyl)guanidine.

24. A compound of claim 1 which is (3S-trans)-5-[[[(6-cyano-3,4-dihydro-3-hydroxy-2,2-dimethyl-2H-1-benzopyran-4-yl)amino]carbonyl]amino]-1,3-dihydro-2H-isoindol-2-carboxylic acid, 2,2,2-trichloroethyl ester.

25. A compound of claim 1 which is (3S-trans)-N-(6-cyano-3,4-dihydro-3-hydroxy-2,2-dimethyl-2H-1-benzopyran-4-yl)-N'-(2,3-dihydro-2-methyl-1H-isoindol-5-yl)urea.

26. A compound of claim 1 which is (3S-trans)-N-(6-cyano-3,4-dihydro-3-hydroxy-2,2-dimethyl-2H-1-benzopyran-4-yl)-N'-(2,3-dihydro-1H-isoindol-5-yl)urea.

27. A compound of claim 1 which is (3S-trans)-N-(6-cyano-3,4-dihydro-3-hydroxy-2,2-dimethyl-2H-1-benzopyran-4-yl)-N'-[3-(3-methyl-5-isoxazoly)phenyl]urea.

28. A compound of claim 1 which is (3S-trans)-N-(6-cyano-3,4-dihydro-3-hydroxy-2,2-dimethyl-2H-1-benzopyran-4-yl)-N'-[3-(1,3-dimethyl-1H-pyrazol-5-yl)phenyl]urea.

29. A compound of claim 1 which is (3S-trans)-N-(6-cyano-3,4-dihydro-3-hydroxy-2,2-dimethyl-2H-1-benzopyran-4-yl)-N'-[3-(1,5-dimethyl-1H-pyrazol-3-yl)phenyl]urea.

30. A compound of claim 1 which is (3S-trans)-N-(6-cyano-3,4-dihydro-3-hydroxy-2,2-dimethyl-2H-1-benzopyran-4-yl)-N'-[3-(5-methyl-3-isoxazoly)phenyl]urea.

31. A compound of claim 1 which is (3S-trans)-N-(6-cyano-3,4-dihydro-3-hydroxy-2,2-dimeth-yl-2H-1-benzopyran-4-yl)-N'-[4-[[methyl(phenylmethyl)amino]methyl]phenyl]urea, monohydrochloride.

32. A compound of claim 1 which is (3S-trans)-N-(6-cyano-3,4-dihydro-3-hydroxy-2,2-dimethyl-2H-1-benzopyran-4-yl)-N-[2,3-dihydro-2-(phenylmethyl)-1H-isoindol-5-yl]urea.

33. A compound of claim 1 which is (3S-trans)-N-(6-cyano-3,4-dihydro-3-hydroxy-2,2-dimethyl-2H-1-benzopyran-4-yl)-N'-[3-[[methyl(phenylmethyl)amino]methyl]phenyl]urea, monohydrochloride.

34. A compound of claim 1 which is (3S-trans)-N-(6-cyano-3,4-dihydro-3-hydroxy-2,2-dimethyl-2H-1-benzopyran-4-yl)-N'-[2-[[methyl(phenylmethyl)amino]methyl]phenyl]urea, monohydrochloride.

35. A compound of claim 1 which is (3S-trans)-N-(6-cyano-3,4-dihydro-3-hydroxy-2,2-dimethyl-2H-1-benzopyran-4-yl)-N'-[3-(5-imidazolyl)phenyl]urea.

36. A compound of claim 1 which is (3S-trans)-N'-(4-chlorophenyl)-N-(6-cyano-3,4-dihydro-3-hydroxy-2,2-dimethyl-2H-1-benzopyran-4-yl)-N-[2-(dimethylamino)]urea.

37. A compound of claim 1 which is (3S-trans)-N'-(4-chlorophenyl)-N-(6-cyano-3,4-dihydro-3-hydroxy-2,2-dimethyl-2H-1-benzopyran-4-yl)-N-[2-(dimethylamino)ethyl]urea.

38. A pharmaceutical composition comprising a compound of claim 1 and a pharmaceutically acceptable career therefor.

39. A method for the treatment of ischemic conditions in a mammalian specie comprising administering to a specie in need thereof an effective amount of the compositions of claim 38.

* * * * *